(12) United States Patent
Plucienniczak et al.

(10) Patent No.: US 8,956,848 B2
(45) Date of Patent: Feb. 17, 2015

(54) UBP1 PROTEASE MUTANT, AND ITS CODING SEQUENCE, THEIR APPLICATION AND METHODS OF PRODUCTION

(75) Inventors: Andrzej Plucienniczak, Warsaw (PL); Anna Wojtowicz, Warsaw (PL); Diana Mikiewicz-Sygula, Czestochowa (PL); Grazyna Plucienniczak, Warsaw (PL)

(73) Assignee: Instytut Biotechnoloii I Antybiotykow, Warsaw (PL)

( * ) Notice: Subject to any disclaimer, the term of this patent is extended or adjusted under 35 U.S.C. 154(b) by 267 days.

(21) Appl. No.: 11/265,532

(22) Filed: Nov. 1, 2005

(65) Prior Publication Data
US 2006/0177845 A1    Aug. 10, 2006

Related U.S. Application Data

(63) Continuation-in-part of application No. PCT/PL2004/000031, filed on Apr. 30, 2004.

(30) Foreign Application Priority Data

May 2, 2003  (PL) .......................................... 359813

(51) Int. Cl.
| | | |
|---|---|---|
| C12Q 1/68 | (2006.01) |
| C12P 21/06 | (2006.01) |
| C12N 9/64 | (2006.01) |
| C07H 21/04 | (2006.01) |
| C12N 9/16 | (2006.01) |

(52) U.S. Cl.
CPC ........................................ *C12N 9/16* (2013.01)
USPC .......... 435/226; 435/219; 435/69.1; 435/69.7; 435/220.1; 435/325; 536/23.2

(58) Field of Classification Search
USPC .......... 530/350; 435/69.1, 6, 226, 325, 320.1, 435/219, 69.7; 536/23.2
See application file for complete search history.

(56) References Cited

PUBLICATIONS

Tobias et al., J. Biol. Chem. 266, 12021-12028 (1991).*

* cited by examiner

*Primary Examiner* — Chih-Min Kam
(74) *Attorney, Agent, or Firm* — Brinks Gilson & Lione

(57) ABSTRACT

A UBP1 protease mutant and the sequence coding it, their application and products and the methods used to produce them may be used in the production of recombinant proteins, particularly on an industrial scale.

8 Claims, 17 Drawing Sheets

```
Atgcagattt tcgtcaaaac tttgaccggt aaaaccataa cattggaagt tgaatcttcc
Gataccatcg acaacgttaa gtcgaaaatt caagacaagg aaggtatccc tccagatcaa
Caaagattga tctttgccgg taagcagcta gaagacggta gaacgctgtc tgattacaac
                                       SacII
Attcagaagg agtccacctt acatcttgtc ttaagactcc gcggtggtGA TTTGTTTATT
GAAAGCAAGA TAAACAGTTT ATTACAATTT TTATTTGGTT CCCGACAGGA TTTTTTGAGA
AATTTTAAAA CTTGGAGTAA CAACAATAAC AATCTATCGA TTTATTTATT AATTTTTGGC
ATAGTAGTAT TTTTTTATAA AAAACCAGAC CATCTAAACT ACATTGTTGA GAGCGTTAGT
GAAATGACAA CAAACTTCAG AAATAATAAT AGCCTTAGCC GTTGGTTGCC CAGAAGTAAG
TTTACCCACT TAGACGAAGA GATCTTGAAA AGAGGTGGTT TCATTGCTGG TTTAGTTAAT
GATGGTAACA CTTGTTTTAT GAACTCTGTT TTGCAATCAT TGGCATCATC CAGAGAATTA
ATGGAGTTCT TGGACAATAA TGTCATAAGG ACCTATGAGG AGATAGAACA AAATGAACAC
AATGAAGAAG GAAACGGGCA AGAATCTGCT CAAGATGAAG CCACTCATAA GAAAAACACT
CGTAAGGGTG GCAAAGTTTA TGGTAAGCAT AAGAAGAAAT TGAATAGGAA GTCAAGTTCG
AAAGAAGACG AAGAAAAGAG CCAGGAGCCA GATATCACTT TCAGTGTCGC CTTAAGGGAT
CTACTTTCTG CCTTAAATGC GAAGTATTAT CGGGATAAAC CCTATTTCAA AACCAATAGT
TTATTGAAAG CAATGTCCAA ATCTCCAAGA AAAAATATTC TTCTTGGCTA CGACCAAGAG
GACGCGCAAG AATTCTTCCA GAACATACTA GCCGAGTTGG AAAGTAACGT TAAATCATTG
AATACTGAAA AACTAGATAC CACTCCAGTT GCGAAATCAG AATTACCCGA TGATGCTTTA
GTAGGTCAAC TTAACCTTGG TGAAGTTGGC ACTGTTTACA TTCCAACTGA ACAGATTGAT
CCTAACTCTA TACTACATGA CAAGTCCATT CAAAATTTCA CACCTTTCAA ACTAATGACT
CCTTTAGATG GTATCACGGC AGAAAGAATT GGTTGTTTAC AGTGTGGTGA GAACGGTGGC
ATAAGATATT CCGTATTTTC GGGATTAAGC TTAAATTTAC CGAACGAGAA TATTGGTTCC
ACTTTAAAAT TATCTCAGTT ATTAAGCGAC TGGAGTAAAC CTGAAATCAT CGAAGGCGTA
GAATGTAACC GTTGTGCCCT CACAGCAGCG CACTCTCATT TATTTGGTCA GTTGAAAGAA
TTTGAAAAAA AACCTGAGGG TTCGATCCCA GAAAAGTTAA TTAACGCTGT AAAAGATAGG
GTCCATCAAA TCGAAGAAGT TCTTGCCAAA CCAGTTATTG ACGATGAAGA TTATAAGAAG
TTGCATACAG CAAATATGGT ACGTAAATGC TCTAAATCTA AGCAGATTTT AATATCAAGA
CCTCCACCAT TATTATCCAT TCATATCAAC AGATCCGTAT TTGATCCAAG AACGTACATG
ATTAGAAAAA ATAACTCGAA AGTATTGTTT AAGTCAAGGT TGAATCTTGC CCCATGGTGT
TGTGATATTA ATGAAATCAA TTTGGATGCT CGTTTGCCAA TGTCAAAAAA GGAAAAAGCT
GCGCAACAAG ATTCAAGTGA AGATGAAAAC ATTGGCGGTG AATACTATAC GAAATTACAT
GAACGCTTCG AGCAGGAATT TGAAGACAGC GAGGAAGAAA AGAATACGA TGACGCAGAG
GGGAACTATG CGTCTCATTA CAATCATACC AAGGATATCA GTAACTATGA TCCCCTAAAC
GGTGAAGTCG ATGGCGTGAC ATCCGATGAT GAAGATGAGT ACATTGAAGA AACCGATGCT
TTAGGGAATA CAATCAAAAA AAGGATCATA GAACATTCTG ATGTTGAAAA CGAGAATGTA
AAAGATAATG AAGAACTGCA AGAAATCGAC AATGTGAGCC TTGACGAACC AAAGATCAAT
GTTGAAGATC AACTAGAAAC ATCATCTGAT GAGGAAGATG TTATACCAGC TCCACCTATC
AATTATGCTA GGTCATTTTC CACAGTTCCA GCCACTCCAT TGACATATTC ATTGCGCTCT
GTCATTGTTC ACTACGGTAC CCATAATTAT GGTCATTACA TTGCATTTAG AAAATACAGG
GGTTGTTGGT GGAGAATATC TGATGAGACT GTGTACGTTG TGGACGAAGC TGAAGTCCTT
TCAACACCCG GTGTATTTAT GTTATTTTAC GAATATGACT TTGATGAAGA AACTGGGAAG
ATGAAGGATG ATTTGGAAGC TATTCAGAGT AATAATGAAG AAGATGATGA AAAAGAGCAG
GAGCAAAAAG GAGTCCAGGA GCCAAAGGAA AGCCAAGAGC AAGGAGAAGG TGAAGAGCAA
GAGGAAGGTC AAGAGCAGAT GAAGTTCGAG AGAACAGAAG ACCATAGAGA TATTTCTGGT
AAAGATGTAA ACTAA
```

Fig. 1

```
atgcagattt tcgtcaaaac tttgaccggt aaaaccataa cattggaagt tgaatcttcc
gataccatcg acaacgttaa gtcgaaaatt caagacaagg aaggtatccc tccagatcaa
caaagattga tctttgccgg taagcagcta gaagacggta gaacgctgtc tgattacaac
attcagaagg agtccacctt acatcttgtc ttaagactcc gcggtggtGA CCATCTAAAC
TACATTGTTG AGAGCGTTAG TGAAATGACA ACAAACTTCA GAAATAATAA TAGCCTTAGC
CGTTGGTTGC CCAGAAGTAA GTTTACCCAC TTAGACGAAG AGATCTTGAA AAGAGGTGGT
TTCATTGCTG GTTTAGTTAA TGATGGTAAC ACTTGTTTTA TGAACTCTGT TTTGCAATCA
TTGGCATCAT CCAGAGAATT AATGGAGTTC TTGGACAATA ATGTCATAAG GACCTATGAG
GAGATAGAAC AAAATGAACA CAATGAAGAA GGAAACGGGC AAGAATCTGC TCAAGATGAA
GCCACTCATA AGAAAAACAC TCGTAAGGGT GGCAAAGTTT ATGGTAAGCA TAAGAAGAAA
TTGAATAGGA AGTCAAGTTC GAAAGAAGAC GAAGAAAAGA GCCAGGAGCC AGATATCACT
TTCAGTGTCG CCTTAAGGGA TCTACTTTCT GCCTTAAATG CGAAGTATTA TCGGGATAAA
CCCTATTTCA AAACCAATAG TTTATTGAAA GCAATGTCCA AATCTCCAAG AAAAAATATT
CTTCTTGGCT ACGACCAAGA GGACGCGCAA GAATTCTTCC AGAACATACT AGCCGAGTTG
GAAAGTAACG TTAAATCATT GAATACTGAA AAACTAGATA CCACTCCAGT TGCGAAATCA
GAATTACCCG ATGATGCTTT AGTAGGTCAA CTTAACCTTG GTGAAGTTGG CACTGTTTAC
ATTCCAACTG AACAGATTGA TCCTAACTCT ATACTACATG ACAAGTCCAT TCAAAATTTC
ACACCTTTCA AACTAATGAC TCCTTTAGAT GGTATCACGG CAGAAAGAAT TGGTTGTTTA
CAGTGTGGTG AGAACGGTGG CATAAGATAT TCCGTATTTT CGGGATTAAG CTTAAATTTA
CCGAACGAGA ATATTGGTTC CACTTTAAAA TTATCTCAGT TATTAAGCGA CTGGAGTAAA
CCTGAAATCA TCGAAGGCGT AGAATGTAAC CGTTGTGCCC TCACAGCAGC GCACTCTCAT
TTATTTGGTC AGTTGAAAGA ATTTGAAAAA AAACCTGAGG GTTCGATCCC AGAAAAGTTA
ATTAACGCTG TAAAAGATAG GGTCCATCAA ATCGAAGAAG TTCTTGCCAA ACCAGTTATT
GACGATGAAG ATTATAAGAA GTTGCATACA GCAAATATGG TACGTAAATG CTCTAAATCT
AAGCAGATTT TAATATCAAG ACCTCCACCA TTATTATCCA TTCATATCAA CAGATCCGTA
TTTGATCCAA GAACGTACAT GATTAGAAAA AATAACTCGA AGTATTGTT TAAGTCAAGG
TTGAATCTTG CCCCATGGTG TTGTGATATT AATGAAATCA ATTTGGATGC TCGTTTGCCA
ATGTCAAAAA AGGAAAAAGC TGCGCAACAA GATTCAAGTG AAGATGAAAA CATTGGCGGT
GAATACTATA CGAAATTACA TGAACGCTTC GAGCAGGAAT TTGAAGACAG CGAGGAAGAA
AAAGAATACG ATGACGCAGA GGGGAACTAT GCGTCTCATT ACAATCATAC CAAGGATATC
AGTAACTATG ATCCCCTAAA CGGTGAAGTC GATGGCGTGA CATCCGATGA TGAAGATGAG
TACATTGAAG AAACCGATGC TTTAGGGAAT ACAATCAAAA AAAGGATCAT AGAACATTCT
GATGTTGAAA ACGAGAATGT AAAAGATAAT GAAGAACTGC AAGAAATCGA CAATGTGAGC
CTTGACGAAC CAAAGATCAA TGTTGAAGAT CAACTAGAAA CATCATCTGA TGAGGAAGAT
GTTATACCAG CTCCACCTAT CAATTATGCT AGGTCATTTT CCACAGTTCC AGCCACTCCA
TTGACATATT CATTGCGCTC TGTCATTGTT CACTACGGTA CCCATAATTA TGGTCATTAC
ATTGCATTTA GAAAATACAG GGGTTGTTGG TGGAGAATAT CTGATGAGAC TGTGTACGTT
GTGGACGAAG CTGAAGTCCT TTCAACACCC GGTGTATTTA TGTTATTTTA CGAATATGAC
TTTGATGAAG AAACTGGGAA GATGAAGGAT GATTTGGAAG CTATTCAGAG TAATAATGAA
GAAGATGATG AAAAAGAGCA GGAGCAAAAA GGAGTCCAGG AGCCAAAGGA AAGCCAAGAG
CAAGGAGAAG GTGAAGAGCA AGAGGAAGGT CAAGAGCAGA TGAAGTTCGA GAGAACAGAA
GACCATAGAG ATATTTCTGG TAAAGATGTA AACTAA
```

Fig. 5

```
  1 mdlfieskin sllqflfgsr qdflrnfktw snnnnnlsiy llifgivvff ykkpdhlnyi
 61 vesvsemttn frnnnslsrw lprskfthld eeilkrggfi ag lvndgntc fmnsvlqsl a
121 ssrelmefld nnvirtyeei eqnehneegn gqesaqdeat hkkntrkggk vygkhkkkln
181 rkssskedee ksqepditfs valrdllsal nakyyrdkpy fktnsllkam sksprknill
241 gydqedaqef fqnilaeles nvkslntekl dttpvaksel pddalvgqln lgevgtvyip
301 teqidpnsil hdksiqnftp fklmtpldgi taerigclqc genggirysv fsglslnlpn
361 enigstlkls qllsdwskpe iiegvecnrc altaahshlf gqlkefekkp egsipekpin
421 avkdrvhqie evlakpvidd edykklhtan mvrkcskskq ilisrpppll sihinrsvfd
481 prtymirknn skvlfksrln lapwccdine inldarlpms kkekaaqqds sedeniggey
541 ytklherfeq efedseeeke yddaegnyas hynhtkdisn ydplngevdg vtsddedeyi
601 eetdalgnti kkriiehsdv enenvkdnee lqeidnvsld epkinvedql etssdeedvi
661 pappinyars fstvpatplt yslrsvivhy gthnyghyia frkyrgcwwr isdetvyvvd
721 eaevlstpgv fmlfy eydfd eetgkmkddl eaiqsnneed dekeqeqkgv qepkesqeqg
781 egeeqeegqe qmkfertedh rdisgkdvn
```

Fig. 6

```
       +1  MetGlnIlePhe ValLysThr  LeuThrGly  LysThrIleThr LeuGluVal  GluSerSer
     1     ATGCAGATTT   TCGTCAAAAC TTTGACCGGT AAAACCATAA   CATTGGAAGT TGAATCTTCC

+1  AspThrIleAsp AsnValLys  SerLysIle  GlnAspLysGlu GlyIlePro  ProAspGln
    61     GATACCATCG   ACAACGTTAA GTCGAAAATT CAAGACAAGG   AAGGTATCCC TCCAGATCAA

+1  GlnArgLeuIle PheAlaGly  LysGlnLeu  GluAspGlyArg ThrLeuSer  AspTyrAsn
   121     CAAAGATTGA   TCTTTGCCGG TAAGCAGCTA GAAGACGGTA   GAACGCTGTC TGATTACAAC

+1  IleGlnLysGlu SerThrLeu  HisLeuVal  LeuArgLeuArg GlyGlyAsp  LeuPheIle
   181     ATTCAGAAGG   AGTCCACCTT ACATCTTGTC TTAAGACTCC   GCGGTGGTGA TTTGTTTATT

+1  GluSerLysIle AsnSerLeu  LeuGlnPhe  LeuPheGlySer ArgGlnAsp  PheLeuArg
   241     GAAAGCAAGA   TAAACAGTTT ATTACAATTT TTATTTGGTT   CCCGACAGGA TTTTTTGAGA

+1  AsnPheLysThr TrpSerAsn  AsnAsnAsn  AsnLeuSerIle TyrLeuLeu  IlePheGly
   301     AATTTTAAAA   CTTGGAGTAA CAACAATAAC AATCTATCGA   TTTATTTATT AATTTTGGC

+1  IleValValPhe PheTyrLys  LysProAsp  HisLeuAsnTyr IleValGlu  SerValSer
   361     ATAGTAGTAT   TTTTTTATAA AAAACCAGAC CATCTAAACT   ACATTGTTGA GAGCGTTAGT

+1  GluMetThrThr AsnPheArg  AsnAsnAsn  SerLeuSerArg TrpLeuPro  ArgSerLys
   421     GAAATGACAA   CAAACTTCAG AAATAATAAT AGCCTTAGCC   GTTGGTTGCC CAGAAGTAAG

+1  PheThrHisLeu AspGluGlu  IleLeuLys  ArgGlyGlyPhe IleAlaGly  LeuValAsn
   481     TTTACCCACT   TAGACGAAGA GATCTTGAAA AGAGGTGGTT   TCATTGCTGG TTTAGTTAAT

+1  AspGlyAsnThr CysPheMet  AsnSerVal  LeuGlnSerLeu AlaSerSer  ArgGluLeu
   541     GATGGTAACA   CTTGTTTTAT GAACTCTGTT TTGCAATCAT   TGGCATCATC CAGAGAATTA

+1  MetGluPheLeu AspAsnAsn  ValIleArg  ThrTyrGluGlu IleGluGln  AsnGluHis
   601     ATGGAGTTCT   TGGACAATAA TGTCATAAGG ACCTATGAGG   AGATAGAACA AAATGAACAC

+1  AsnGluGluGly AsnGlyGln  GluSerAla  GlnAspGluAla ThrHisLys  LysAsnThr
   661     AATGAAGAAG   GAAACGGGCA AGAATCTGCT CAAGATGAAG   CCACTCATAA GAAAAACACT

+1  ArgLysGlyGly LysValTyr  GlyLysHis  LysLysLysLeu AsnArgLys  SerSerSer
   721     CGTAAGGGTG   GCAAAGTTTA TGGTAAGCAT AAGAAGAAAT   TGAATAGGAA GTCAAGTTCG

+1  LysGluAspGlu GluLysSer  GlnGluPro  AspIleThrPhe SerValAla  LeuArgAsp
   781     AAAGAAGACG   AAGAAAAGAG CCAGGAGCCA GATATCACTT   TCAGTGTCGC CTTAAGGGAT

+1  LeuLeuSerAla LeuAsnAla  LysTyrTyr  ArgAspLysPro TyrPheLys  ThrAsnSer
   841     CTACTTTCTG   CCTTAAATGC GAAGTATTAT CGGGATAAAC   CCTATTTCAA AACCAATAGT

+1  LeuLeuLysAla MetSerLys  SerProArg  LysAsnIleLeu LeuGlyTyr  AspGlnGlu
   901     TTATTGAAAG   CAATGTCCAA ATCTCCAAGA AAAAATATTC   TTCTTGGCTA CGACCAAGAG

+1  AspAlaGlnGlu PhePheGln  AsnIleLeu  AlaGluLeuGlu SerAsnVal  LysSerLeu
   961     GACGCGCAAG   AATTCTTCCA GAACATACTA GCCGAGTTGG   AAAGTAACGT TAAATCATTG

+1  AsnThrGluLys LeuAspThr  ThrProVal  AlaLysSerGlu LeuProAsp  AspAlaLeu
  1021     AATACTGAAA   AACTAGATAC CACTCCAGTT GCGAAATCAG   AATTACCCGA TGATGCTTTA

+1  ValGlyGlnLeu AsnLeuGly  GluValGly  ThrValTyrIle ProThrGlu  GlnIleAsp
  1081     GTAGGTCAAC   TTAACCTTGG TGAAGTTGGC ACTGTTTACA   TTCCAACTGA ACAGATTGAT
```

Fig. 8

```
      +1 ProAsnSerIle LeuHisAsp LysSerIle GlnAsnPheThr ProPheLys LeuMetThr
    1141 CCTAACTCTA TACTACATGA CAAGTCCATT CAAAATTTCA CACCTTTCAA ACTAATGACT

+1 ProLeuAspGly IleThrAla GluArgIle GlyCysLeuGln CysGlyGlu AsnGlyGly
    1201 CCTTTAGATG GTATCACGGC AGAAAGAATT GGTTGTTTAC AGTGTGGTGA GAACGGTGGC

+1 IleArgTyrSer ValPheSer GlyLeuSer LeuAsnLeuPro AsnGluAsn IleGlySer
    1261 ATAAGATATT CCGTATTTTC GGGATTAAGC TTAAATTTAC CGAACGAGAA TATTGGTTCC

+1 ThrLeuLysLeu SerGlnLeu LeuSerAsp TrpSerLysPro GluIleIle GluGlyVal
    1321 ACTTTAAAAT TATCTCAGTT ATTAAGCGAC TGGAGTAAAC CTGAAATCAT CGAAGGCGTA

+1 GluCysAsnArg CysAlaLeu ThrAlaAla HisSerHisLeu PheGlyGln LeuLysGlu
    1381 GAATGTAACC GTTGTGCCCT CACAGCAGCG CACTCTCATT TATTTGGTCA GTTGAAAGAA

+1 PheGluLysLys ProGluGly SerIlePro GluLysLeuIle AsnAlaVal LysAspArg
    1441 TTTGAAAAAA AACCTGAGGG TTCGATCCCA GAAAAGTTAA TTAACGCTGT AAAAGATAGG

+1 ValHisGlnIle GluGluVal LeuAlaLys ProValIleAsp AspGluAsp TyrLysLys
    1501 GTCCATCAAA TCGAAGAAGT TCTTGCCAAA CCAGTTATTG ACGATGAAGA TTATAAGAAG

+1 LeuHisThrAla AsnMetVal ArgLysCys SerLysSerLys GlnIleLeu IleSerArg
    1561 TTGCATACAG CAAATATGGT ACGTAAATGC TCTAAATCTA AGCAGATTTT AATATCAAGA

+1 ProProProLeu LeuSerIle HisIleAsn ArgSerValPhe AspProArg ThrTyrMet
    1621 CCTCCACCAT TATTATCCAT TCATATCAAC AGATCCGTAT TTGATCCAAG AACGTACATG

+1 IleArgLysAsn AsnSerLys ValLeuPhe LysSerArgLeu AsnLeuAla ProTrpCys
    1681 ATTAGAAAAA ATAACTCGAA AGTATTGTTT AAGTCAAGGT TGAATCTTGC CCCATGGTGT

+1 CysAspIleAsn GluIleAsn LeuAspAla ArgLeuProMet SerLysLys GluLysAla
    1741 TGTGATATTA ATGAAATCAA TTTGGATGCT CGTTTGCCAA TGTCAAAAAA GGAAAAAGCT

+1 AlaGlnGlnAsp SerSerGlu AspGluAsn IleGlyGlyGlu TyrTyrThr LysLeuHis
    1801 GCGCAACAAG ATTCAAGTGA AGATGAAAAC ATTGGCGGTG AATACTATAC GAAATTACAT

+1 GluArgPheGlu GlnGluPhe GluAspSer GluGluGluLys GluTyrAsp AspAlaGlu
    1861 GAACGCTTCG AGCAGGAATT TGAAGACAGC GAGGAAGAAA AAGAATACGA TGACGCAGAG

+1 GlyAsnTyrAla SerHisTyr AsnHisThr LysAspIleSer AsnTyrAsp ProLeuAsn
    1921 GGGAACTATG CGTCTCATTA CAATCATACC AAGGATATCA GTAACTATGA TCCCCTAAAC

+1 GlyGluValAsp GlyValThr SerAspAsp GluAspGluTyr IleGluGlu ThrAspAla
    1981 GGTGAAGTCG ATGGCGTGAC ATCCGATGAT GAAGATGAGT ACATTGAAGA AACCGATGCT

+1 LeuGlyAsnThr IleLysLys ArgIleIle GluHisSerAsp ValGluAsn GluAsnVal
    2041 TTAGGGAATA CAATCAAAAA AAGGATCATA GAACATTCTG ATGTTGAAAA CGAGAATGTA

+1 LysAspAsnGlu GluLeuGln GluIleAsp AsnValSerLeu AspGluPro LysIleAsn
    2101 AAAGATAATG AAGAACTGCA AGAAATCGAC AATGTGAGCC TTGACGAACC AAAGATCAAT

+1 ValGluAspGln LeuGluThr SerSerAsp GluGluAspVal IleProAla ProProIle
    2161 GTTGAAGATC AACTAGAAAC ATCATCTGAT GAGGAAGATG TTATACCAGC TCCACCTATC

+1 AsnTyrAlaArg SerPheSer ThrValPro AlaThrProLeu ThrTyrSer LeuArgSer
    2221 AATTATGCTA GGTCATTTTC CACAGTTCCA GCCACTCCAT TGACATATTC ATTGCGCTCT
```

Fig. 8 cont.

```
     +1 ValIleValHis TyrGlyThr HisAsnTyr GlyHisTyrIle AlaPheArg LysTyrArg
   2281 GTCATTGTTC ACTACGGTAC CCATAATTAT GGTCATTACA TTGCATTTAG AAAATACAGG

+1 GlyCysTrpTrp ArgIleSer AspGluThr ValTyrValVal AspGluAla GluValLeu
   2341 GGTTGTTGGT GGAGAATATC TGATGAGACT GTGTACGTTG TGGACGAAGC TGAAGTCCTT

+1 SerThrProGly ValPheMet LeuPheTyr GluTyrAspLeu AspGluGlu ThrGlyLys
   2401 TCAACACCCG GTGTATTTAT GTTATTTTAC GAATATGACC TTGATGAAGA AACTGGGAAG

+1 MetLysAspAsp LeuGluAla IleLeuSer AsnAsnGluGlu AspAspGlu LysGluGln
   2461 ATGAAGGATG ATTTGGAAGC TATTCTGAGT AATAATGAAG AAGATGATGA AAAAGAGCAG

+1 GluGlnLysGly ValGlnGlu ProLysGlu SerGlnGluGln GlyGluGly GluGluGln
   2521 GAGCAAAAAG GAGTCCAGGA GCCAAAGGAA AGCCAAGAGC AAGGAGAAGG TGAAGAGCAA

+1 GluGluGlyGln GluGlnMet LysPheGlu ArgThrGluAsp HisArgAsp IleSerGly
   2581 GAGGAAGGTC AAGAGCAGAT GAAGTTCGAG AGAACAGAAG ACCATAGAGA TATTTCTGGT

+1 LysAspValAsn ***
   2641 AAAGATGTAA ACTAA
```

Fig. 8 cont.

```
    +1  MetGlnIlePhe ValLysThr LeuThrGly LysThrIleThr LeuGluVal GluSerSer
     1  ATGCAGATTT TCGTCAAAAC TTTGACCGGT AAAACCATAA CATTGGAAGT TGAATCTTCC

+1  AspThrIleAsp AsnValLys SerLysIle GlnAspLysGlu GlyIlePro ProAspGln
    61  GATACCATCG ACAACGTTAA GTCGAAAATT CAAGACAAGG AAGGTATCCC TCCAGATCAA

+1  GlnArgLeuIle PheAlaGly LysGlnLeu GluAspGlyArg ThrLeuSer AspTyrAsn
   121  CAAAGATTGA TCTTTGCCGG TAAGCAGCTA GAAGACGGTA GAACGCTGTC TGATTACAAC

+1  IleGlnLysGlu SerThrLeu HisLeuVal LeuArgLeuArg GlyGlyAsp LeuPheIle
   181  ATTCAGAAGG AGTCCACCTT ACATCTTGTC TTAAGACTCC GCGGTGGTGA TTTGTTTATT

+1  GluSerLysIle AsnSerLeu LeuGlnPhe LeuPheGlySer ArgGlnAsp PheLeuArg
   241  GAAAGCAAGA TAAACAGTTT ATTACAATTT TTATTTGGTT CCCGACAGGA TTTTTTGAGA

+1  AsnPheLysThr TrpSerAsn AsnAsnAsn AsnLeuSerIle TyrLeuLeu IlePheGly
   301  AATTTTAAAA CTTGGAGTAA CAACAATAAC AATCTATCGA TTATTTATT AATTTTTGGC

+1  IleValValPhe PheTyrLys LysProAsp HisLeuAsnTyr IleValGlu SerValSer
   361  ATAGTAGTAT TTTTTTATAA AAAACCAGAC CATCTAAACT ACATTGTTGA GAGCGTTAGT

+1  GluMetThrThr AsnPheArg AsnAsnAsn SerLeuSerArg TrpLeuPro ArgSerLys
   421  GAAATGACAA CAAACTTCAG AAATAATAAT AGCCTTAGCC GTTGGTTGCC CAGAAGTAAG

+1  PheThrHisLeu AspGluGlu IleLeuLys ArgGlyGlyPhe IleAlaGly LeuValAsn
   481  TTTACCCACT TAGACGAAGA GATCTTGAAA AGAGGTGGTT TCATTGCTGG TTTAGTTAAT

+1  AspGlyAsnThr CysPheMet AsnSerVal LeuGlnSerLeu AlaSerSer ArgGluLeu
   541  GATGGTAACA CTTGTTTTAT GAACTCTGTT TTGCAATCAT TGGCATCATC CAGAGAATTA

+1  MetGluPheLeu AspAsnAsn ValIleArg ThrTyrGluGlu IleGluGln AsnGluHis
   601  ATGGAGTTCT TGGACAATAA TGTCATAAGG ACCTATGAGG AGATAGAACA AAATGAACAC

+1  AsnGluGluGly AsnGlyGln GluSerAla GlnAspGluAla ThrHisLys LysAsnThr
   661  AATGAAGAAG GAAACGGGCA AGAATCTGCT CAAGATGAAG CCACTCATAA GAAAAACACT

+1  ArgLysGlyGly LysValTyr GlyLysHis LysLysLysLeu AsnArgLys SerSerSer
   721  CGTAAGGGTG GCAAAGTTTA TGGTAAGCAT AAGAAGAAAT TGAATAGGAA GTCAAGTTCG

+1  LysGluAspGlu GluLysSer GlnGluPro AspIleThrPhe SerValAla LeuArgAsp
   781  AAAGAAGACG AAGAAAAGAG CCAGGAGCCA GATATCACTT TCAGTGTCGC CTTAAGGGAT

+1  LeuLeuSerAla LeuAsnAla LysTyrTyr ArgAspLysPro TyrPheLys ThrAsnSer
   841  CTACTTTCTG CCTTAAATGC GAAGTATTAT CGGGATAAAC CCTATTTCAA AACCAATAGT

+1  LeuLeuLysAla MetSerLys SerProArg LysAsnIleLeu LeuGlyTyr AspGlnGlu
   901  TTATTGAAAG CAATGTCCAA ATCTCCAAGA AAAAATATTC TTCTTGGCTA CGACCAAGAG

+1  AspAlaGlnGlu PhePheGln AsnIleLeu AlaGluLeuGlu SerAsnVal LysSerLeu
   961  GACGCGCAAG AATTCTTCCA GAACATACTA GCCGAGTTGG AAAGTAACGT TAAATCATTG

+1  AsnThrGluLys LeuAspThr ThrProVal AlaLysSerGlu LeuProAsp AspAlaLeu
  1021  AATACTGAAA AACTAGATAC CACTCCAGTT GCGAAATCAG AATTACCCGA TGATGCTTTA

+1  ValGlyGlnLeu AsnLeuGly GluValGly ThrValTyrIle ProThrGlu GlnIleAsp
  1081  GTAGGTCAAC TTAACCTTGG TGAAGTTGGC ACTGTTTACA TTCCAACTGA ACAGATTGAT
```

Fig. 9

```
      +1 ProAsnSerIle LeuHisAsp LysSerIle GlnAsnPheThr ProPheLys LeuMetThr
1141     CCTAACTCTA TACTACATGA CAAGTCCATT CAAAATTTCA CACCTTTCAA ACTAATGACT

+1 ProLeuAspGly IleThrAla GluArgIle GlyCysLeuGln CysGlyGlu AsnGlyGly
1201     CCTTTAGATG GTATCACGGC AGAAAGAATT GGTTGTTTAC AGTGTGGTGA GAACGGTGGC

+1 IleArgTyrSer ValPheSer GlyLeuSer LeuAsnLeuPro AsnGluAsn IleGlySer
1261     ATAAGATATT CCGTATTTTC GGGATTAAGC TTAAATTTAC CGAACGAGAA TATTGGTTCC

+1 ThrLeuLysLeu SerGlnLeu LeuSerAsp TrpSerLysPro GluIleIle GluGlyVal
1321     ACTTTAAAAT TATCTCAGTT ATTAAGCGAC TGGAGTAAAC CTGAAATCAT CGAAGGCGTA

+1 GluCysAsnArg CysAlaLeu ThrAlaAla HisSerHisLeu PheGlyGln LeuLysGlu
1381     GAATGTAACC GTTGTGCCCT CACAGCAGCG CACTCTCATT TATTTGGTCA GTTGAAAGAA

+1 PheGluLysLys ProGluGly SerIlePro GluLysProIle AsnAlaVal LysAspArg
1441     TTTGAAAAAA AACCTGAGGG TTCGATCCCA GAAAAGCCAA TTAACGCTGT AAAAGATAGG

+1 ValHisGlnIle GluGluVal LeuAlaLys ProValIleAsp AspGluAsp TyrLysLys
1501     GTCCATCAAA TCGAAGAAGT TCTTGCCAAA CCAGTTATTG ACGATGAAGA TTATAAGAAG

+1 LeuHisThrAla AsnMetVal ArgLysCys SerLysSerLys GlnIleLeu IleSerArg
1561     TTGCATACAG CAAATATGGT ACGTAAATGC TCTAAATCTA AGCAGATTTT AATATCAAGA

+1 ProProProLeu LeuSerIle HisIleAsn ArgSerValPhe AspProArg ThrTyrMet
1621     CCTCCACCAT TATTATCCAT TCATATCAAC AGATCCGTAT TTGATCCAAG AACGTACATG

+1 IleArgLysAsn AsnSerLys ValLeuPhe LysSerArgLeu AsnLeuAla ProTrpCys
1681     ATTAGAAAAA ATAACTCGAA AGTATTGTTT AAGTCAAGGT TGAATCTTGC CCCATGGTGT

+1 CysAspIleAsn GluIleAsn LeuAspAla ArgLeuProMet SerLysLys GluLysAla
1741     TGTGATATTA ATGAAATCAA TTTGGATGCT CGTTTGCCAA TGTCAAAAAA GGAAAAAGCT

+1 AlaGlnGlnAsp SerSerGlu AspGluAsn IleGlyGlyGlu TyrTyrThr LysLeuHis
1801     GCGCAACAAG ATTCAAGTGA AGATGAAAAC ATTGGCGGTG AATACTATAC GAAATTACAT

+1 GluArgPheGlu GlnGluPhe GluAspSer GluGluGluLys GluTyrAsp AspAlaGlu
1861     GAACGCTTCG AGCAGGAATT TGAAGACAGC GAGGAAGAAA AAGAATACGA TGACGCAGAG

+1 GlyAsnTyrAla SerHisTyr AsnHisThr LysAspIleSer AsnTyrAsp ProLeuAsn
1921     GGGAACTATG CGTCTCATTA CAATCATACC AAGGATATCA GTAACTATGA TCCCCTAAAC

+1 GlyGluValAsp GlyValThr SerAspAsp GluAspGluTyr IleGluGlu ThrAspAla
1981     GGTGAAGTCG ATGGCGTGAC ATCCGATGAT GAAGATGAGT ACATTGAAGA AACCGATGCT

+1 LeuGlyAsnThr IleLysLys ArgIleIle GluHisSerAsp ValGluAsn GluAsnVal
2041     TTAGGGAATA CAATCAAAAA AAGGATCATA GAACATTCTG ATGTTGAAAA CGAGAATGTA

+1 LysAspAsnGlu GluLeuGln GluIleAsp AsnValSerLeu AspGluPro LysIleAsn
2101     AAAGATAATG AAGAACTGCA AGAAATCGAC AATGTGAGCC TTGACGAACC AAAGATCAAT

+1 ValGluAspGln LeuGluThr SerSerAsp GluGluAspVal IleProAla ProProIle
2161     GTTGAAGATC AACTAGAAAC ATCATCTGAT GAGGAAGATG TTATACCAGC TCCACCTATC

+1 AsnTyrAlaArg SerPheSer ThrValPro AlaThrProLeu ThrTyrSer LeuArgSer
2221     AATTATGCTA GGTCATTTTC CACAGTTCCA GCCACTCCAT TGACATATTC ATTGCGCTCT
```

Fig. 9 cont.

```
     +1 ValIleValHis TyrGlyThr HisAsnTyr GlyHisTyrIle AlaPheArg LysTyrArg
2281    GTCATTGTTC ACTACGGTAC CCATAATTAT GGTCATTACA TTGCATTTAG AAAATACAGG

+1 GlyCysTrpTrp ArgIleSer AspGluThr ValTyrValVal AspGluAla GluValLeu
2341    GGTTGTTGGT GGAGAATATC TGATGAGACT GTGTACGTTG TGGACGAAGC TGAAGTCCTT

+1 SerThrProGly ValPheMet LeuPheTyr GluTyrAspLeu AspGluGlu ThrGlyLys
2401    TCAACACCCG GTGTATTTAT GTTATTTTAC GAATATGACC TTGATGAAGA AACTGGGAAG

+1 MetLysAspAsp LeuGluAla IleLeuSer AsnAsnGluGlu AspAspGlu LysGluGln
2461    ATGAAGGATG ATTTGGAAGC TATTCTGAGT AATAATGAAG AAGATGATGA AAAAGAGCAG

+1 GluGlnLysGly ValGlnGlu ProLysGlu SerGlnGluGln GlyGluGly GluGluGln
2521    GAGCAAAAAG GAGTCCAGGA GCCAAAGGAA AGCCAAGAGC AAGGAGAAGG TGAAGAGCAA

+1 GluGluGlyGln GluGlnMet LysPheGlu ArgThrGluAsp HisArgAsp IleSerGly
2581    GAGGAAGGTC AAGAGCAGAT GAAGTTCGAG AGAACAGAAG ACCATAGAGA TATTTCTGGT

+1 LysAspValAsn ***
2641    AAAGATGTAA ACTAA
```

Fig. 9 cont.

```
     +1  MetGlnIlePhe ValLysThr LeuThrGly  LysThrIleThr LeuGluVal GluSerSer
      1  ATGCAGATTT  TCGTCAAAAC TTTGACCGGT  AAAACCATAA  CATTGGAAGT TGAATCTTCC

+1  AspThrIleAsp AsnValLys SerLysIle  GlnAspLysGlu GlyIlePro ProAspGln
     61  GATACCATCG  ACAACGTTAA GTCGAAAATT  CAAGACAAGG  AAGGTATCCC TCCAGATCAA

+1  GlnArgLeuIle PheAlaGly LysGlnLeu  GluAspGlyArg ThrLeuSer AspTyrAsn
    121  CAAAGATTGA  TCTTTGCCGG TAAGCAGCTA  GAAGACGGTA  GAACGCTGTC TGATTACAAC

+1  IleGlnLysGlu SerThrLeu HisLeuVal  LeuArgLeuArg GlyGlyAsp LeuPheIle
    181  ATTCAGAAGG  AGTCCACCTT ACATCTTGTC  TTAAGACTCC  GCGGTGGTGA TTTGTTTATT

+1  GluSerLysIle AsnSerLeu LeuGlnPhe  LeuPheGlySer ArgGlnAsp PheLeuArg
    241  GAAAGCAAGA  TAAACAGTTT ATTACAATTT  TTATTTGGTT  CCCGACAGGA TTTTTTGAGA

+1  AsnPheLysThr TrpSerAsn AsnAsnAsn  AsnLeuSerIle TyrLeuLeu IlePheGly
    301  AATTTTAAAA  CTTGGAGTAA CAACAATAAC  AATCTATCGA  TTTATTTATT AATTTTGGC

+1  IleValValPhe PheTyrLys LysProAsp  HisLeuAsnTyr IleValGlu SerValSer
    361  ATAGTAGTAT  TTTTTTATAA AAAACCAGAC  CATCTAAACT  ACATTGTTGA GAGCGTTAGT

+1  GluMetThrThr AsnPheArg AsnAsnAsn  SerLeuSerArg TrpLeuPro ArgSerLys
    421  GAAATGACAA  CAAACTTCAG AAATAATAAT  AGCCTTAGCC  GTTGGTTGCC CAGAAGTAAG

+1  PheThrHisLeu AspGluGlu IleLeuLys  ArgGlyGlyPhe IleAlaGly LeuValAsn
    481  TTTACCCACT  TAGACGAAGA GATCTTGAAA  AGAGGTGGTT  TCATTGCTGG TTTAGTTAAT

+1  AspGlyAsnThr CysPheMet AsnSerVal  LeuGlnSerLeu AlaSerSer ArgGluLeu
    541  GATGGTAACA  CTTGTTTTAT GAACTCTGTT  TTGCAATCAT  TGGCATCATC CAGAGAATTA

+1  MetGluPheLeu AspAsnAsn ValIleArg  ThrTyrGluGlu IleGluGln AsnGluHis
    601  ATGGAGTTCT  TGGACAATAA TGTCATAAGG  ACCTATGAGG  AGATAGAACA AAATGAACAC

+1  AsnGluGluGly AsnGlyGln GluSerAla  GlnAspGluAla ThrHisLys LysAsnThr
    661  AATGAAGAAG  GAAACGGGCA AGAATCTGCT  CAAGATGAAG  CCACTCATAA GAAAAACACT

+1  ArgLysGlyGly LysValTyr GlyLysHis  LysLysLysLeu AsnArgLys SerSerSer
    721  CGTAAGGGTG  GCAAAGTTTA TGGTAAGCAT  AAGAAGAAAT  TGAATAGGAA GTCAAGTTCG

+1  LysGluAspGlu GluLysSer GlnGluPro  AspIleThrPhe SerValAla LeuArgAsp
    781  AAAGAAGACG  AAGAAAAGAG CCAGGAGCCA  GATATCACTT  TCAGTGTCGC CTTAAGGGAT

+1  LeuLeuSerAla LeuAsnAla LysTyrTyr  ArgAspLysPro TyrPheLys ThrAsnSer
    841  CTACTTTCTG  CCTTAAATGC AAGTATTAT  CGGGATAAAC  CCTATTTCAA AACCAATAGT

+1  LeuLeuLysAla MetSerLys SerProArg  LysAsnIleLeu LeuGlyTyr AspGlnGlu
    901  TTATTGAAAG  CAATGTCCAA ATCTCCAAGA  AAAAATATTC  TTCTTGGCTA CGACCAAGAG

+1  AspAlaGlnGlu PhePheGln AsnIleLeu  AlaGluLeuGlu SerAsnVal LysSerLeu
    961  GACGCGCAAG  AATTCTTCCA GAACATACTA  GCCGAGTTGG  AAAGTAACGT TAAATCATTG

+1  AsnThrGluLys LeuAspThr ThrProVal  AlaLysSerGlu LeuProAsp AspAlaLeu
   1021  AATACTGAAA  AACTAGATAC CACTCCAGTT  GCGAAATCAG  AATTACCCGA TGATGCTTTA

+1  ValGlyGlnLeu AsnLeuGly GluValGly  ThrValTyrIle ProThrGlu GlnIleAsp
   1081  GTAGGTCAAC  TTAACCTTGG TGAAGTTGGC  ACTGTTTACA  TTCCAACTGA ACAGATTGAT
                                   Fig. 10
```

```
      +1  ProAsnSerIle LeuHisAsp LysSerIle GlnAsnPheThr ProPheLys LeuMetThr
    1141  CCTAACTCTA TACTACATGA CAAGTCCATT CAAAATTTCA CACCTTTCAA ACTAATGACT

+1  ProLeuAspGly IleThrAla GluArgIle GlyCysLeuGln CysGlyGlu AsnGlyGly
    1201  CCTTTAGATG GTATCACGGC AGAAAGAATT GGTTGTTTAC AGTGTGGTGA GAACGGTGGC

+1  IleArgTyrSer ValPheSer GlyLeuSer LeuAsnLeuPro AsnGluAsn IleGlySer
    1261  ATAAGATATT CCGTATTTTC GGGATTAAGC TTAAATTTAC CGAACGAGAA TATTGGTTCC

+1  ThrLeuLysLeu SerGlnLeu LeuSerAsp TrpSerLysPro GluIleIle GluGlyVal
    1321  ACTTTAAAAT TATCTCAGTT ATTAAGCGAC TGGAGTAAAC CTGAAATCAT CGAAGGCGTA

+1  GluCysAsnArg CysAlaLeu ThrAlaAla HisSerHisLeu PheGlyGln LeuLysGlu
    1381  GAATGTAACC GTTGTGCCCT CACAGCAGCG CACTCTCATT TATTTGGTCA GTTGAAAGAA

+1  PheGluLysLys ProGluGly SerIlePro GluLysProIle AsnAlaVal LysAspArg
    1441  TTTGAAAAAA AACCTGAGGG TTCGATCCCA GAAAAGCCAA TTAACGCTGT AAAAGATAGG

+1  ValHisGlnIle GluGluVal LeuAlaLys ProValIleAsp AspGluAsp TyrLysLys
    1501  GTCCATCAAA TCGAAGAAGT TCTTGCCAAA CCAGTTATTG ACGATGAAGA TTATAAGAAG

+1  LeuHisThrAla AsnMetVal ArgLysCys SerLysSerLys GlnIleLeu IleSerArg
    1561  TTGCATACAG CAAATATGGT ACGTAAATGC TCTAAATCTA AGCAGATTTT AATATCAAGA

+1  ProProProLeu LeuSerIle HisIleAsn ArgSerValPhe AspProArg ThrTyrMet
    1621  CCTCCACCAT TATTATCCAT TCATATCAAC AGATCCGTAT TTGATCCAAG AACGTACATG

+1  IleArgLysAsn AsnSerLys ValLeuPhe LysSerArgLeu AsnLeuAla ProTrpCys
    1681  ATTAGAAAAA ATAACTCGAA AGTATTGTTT AAGTCAAGGT TGAATCTTGC CCCATGGTGT

+1  CysAspIleAsn GluIleAsn LeuAspAla ArgLeuProMet SerLysLys GluLysAla
    1741  TGTGATATTA ATGAAATCAA TTTGGATGCT CGTTTGCCAA TGTCAAAAAA GGAAAAAGCT

+1  AlaGlnGlnAsp SerSerGlu AspGluAsn IleGlyGlyGlu TyrTyrThr LysLeuHis
    1801  GCGCAACAAG ATTCAAGTGA AGATGAAAAC ATTGGCGGTG AATACTATAC GAAATTACAT

+1  GluArgPheGlu GlnGluPhe GluAspSer GluGluGluLys GluTyrAsp AspAlaGlu
    1861  GAACGCTTCG AGCAGGAATT TGAAGACAGC GAGGAAGAAA AGAATACGA TGACGCAGAG

+1  GlyAsnTyrAla SerHisTyr AsnHisThr LysAspIleSer AsnTyrAsp ProLeuAsn
    1921  GGGAACTATG CGTCTCATTA CAATCATACC AAGGATATCA GTAACTATGA TCCCCTAAAC

+1  GlyGluValAsp GlyValThr SerAspAsp GluAspGluTyr IleGluGlu ThrAspAla
    1981  GGTGAAGTCG ATGGCGTGAC ATCCGATGAT GAAGATGAGT ACATTGAAGA AACCGATGCT

+1  LeuGlyAsnThr IleLysLys ArgIleIle GluHisSerAsp ValGluAsn GluAsnVal
    2041  TTAGGGAATA CAATCAAAAA AAGGATCATA GAACATTCTG ATGTTGAAAA CGAGAATGTA

+1  LysAspAsnGlu GluLeuGln GluIleAsp AsnValSerLeu AspGluPro LysIleAsn
    2101  AAAGATAATG AAGAACTGCA AGAAATCGAC AATGTGAGCC TTGACGAACC AAAGATCAAT

+1  ValGluAspGln LeuGluThr SerSerAsp GluGluAspVal IleProAla ProProIle
    2161  GTTGAAGATC AACTAGAAAC ATCATCTGAT GAGGAAGATG TTATACCAGC TCCACCTATC

+1  AsnTyrAlaArg SerPheSer ThrValPro AlaThrProLeu ThrTyrSer LeuArgSer
    2221  AATTATGCTA GGTCATTTTC CACAGTTCCA GCCACTCCAT TGACATATTC ATTGCGCTCT
                                    Fig. 10 cont.
```

```
      +1  ValIleValHis TyrGlyThr HisAsnTyr GlyHisTyrIle AlaPheArg LysTyrArg
    2281  GTCATTGTTC  ACTACGGTAC CCATAATTAT GGTCATTACA  TTGCATTTAG AAAATACAGG

+1  GlyCysTrpTrp ArgIleSer AspGluThr ValTyrValVal AspGluAla GluValLeu
    2341  GGTTGTTGGT  GGAGAATATC TGATGAGACT GTGTACGTTG  TGGACGAAGC TGAAGTCCTT

+1  SerThrProGly ValPheMet LeuPheTyr GluTyrAspPhe AspGluGlu ThrGlyLys
    2401  TCAACACCCG  GTGTATTTAT GTTATTTTAC GAATATGACT  TTGATGAAGA AACTGGGAAG

+1  MetLysAspAsp LeuGluAla IleLeuSer AsnAsnGluGlu AspAspGlu LysGluGln
    2461  ATGAAGGATG  ATTTGGAAGC TATTCTGAGT AATAATGAAG  AAGATGATGA AAAAGAGCAG

+1  GluGlnLysGly ValGlnGlu ProLysGlu SerGlnGluGln GlyGluGly GluGluGln
    2521  GAGCAAAAAG  GAGTCCAGGA GCCAAAGGAA AGCCAAGAGC  AAGGAGAAGG TGAAGAGCAA

+1  GluGluGlyGln GluGlnMet LysPheGlu ArgThrGluAsp HisArgAsp IleSerGly
    2581  GAGGAAGGTC  AAGAGCAGAT GAAGTTCGAG AGAACAGAAG  ACCATAGAGA TATTTCTGGT

+1  LysAspValAsn ***
    2641  AAAGATGTAA  ACTAA
```

Fig. 10 cont.

SEQUENCE LISTING

<160> NUMBER OF SEQ ID NOS: 15

<210> SEQ ID NO 1
<211> LENGTH: 2655
<212> TYPE: DNA
<213> ORGANISM: artificial sequence
<220> FEATURE:
<223> OTHER INFORMATION: Ubiquitin::UBP1
<220> FEATURE:
<221> NAME/KEY: CDS
<222> LOCATION: (1)..(2655)
<223> OTHER INFORMATION: sequence coding the hybrid protein Ubiquitin::
       UBP1

<400> SEQUENCE: 1

| | | | | | | | | | | | | | | | | |
|---|---|---|---|---|---|---|---|---|---|---|---|---|---|---|---|---|
| atg | cag | att | ttc | gtc | aaa | act | ttg | acc | ggt | aaa | acc | ata | aca | ttg | gaa | 48 |
| Met | Gln | Ile | Phe | Val | Lys | Thr | Leu | Thr | Gly | Lys | Thr | Ile | Thr | Leu | Glu | |
| 1 | | | | 5 | | | | | 10 | | | | | 15 | | |

| gtt | gaa | tct | tcc | gat | acc | atc | gac | aac | gtt | aag | tcg | aaa | att | caa | gac | 96 |
|---|---|---|---|---|---|---|---|---|---|---|---|---|---|---|---|---|
| Val | Glu | Ser | Ser | Asp | Thr | Ile | Asp | Asn | Val | Lys | Ser | Lys | Ile | Gln | Asp | |
| | | | 20 | | | | | 25 | | | | | 30 | | | |

| aag | gaa | ggt | atc | cct | cca | gat | caa | caa | aga | ttg | atc | ttt | gcc | ggt | aag | 144 |
|---|---|---|---|---|---|---|---|---|---|---|---|---|---|---|---|---|
| Lys | Glu | Gly | Ile | Pro | Pro | Asp | Gln | Gln | Arg | Leu | Ile | Phe | Ala | Gly | Lys | |
| | | 35 | | | | | 40 | | | | | 45 | | | | |

| cag | cta | gaa | gac | ggt | aga | acg | ctg | tct | gat | tac | aac | att | cag | aag | gag | 192 |
|---|---|---|---|---|---|---|---|---|---|---|---|---|---|---|---|---|
| Gln | Leu | Glu | Asp | Gly | Arg | Thr | Leu | Ser | Asp | Tyr | Asn | Ile | Gln | Lys | Glu | |
| | 50 | | | | | 55 | | | | | 60 | | | | | |

| tcc | acc | tta | cat | ctt | gtc | tta | aga | ctc | cgc | ggt | ggt | gat | ttg | ttt | att | 240 |
|---|---|---|---|---|---|---|---|---|---|---|---|---|---|---|---|---|
| Ser | Thr | Leu | His | Leu | Val | Leu | Arg | Leu | Arg | Gly | Gly | Asp | Leu | Phe | Ile | |
| 65 | | | | | 70 | | | | | 75 | | | | | 80 | |

| gaa | agc | aag | ata | aac | agt | tta | tta | caa | ttt | tta | ttt | ggt | tcc | cga | cag | 288 |
|---|---|---|---|---|---|---|---|---|---|---|---|---|---|---|---|---|
| Glu | Ser | Lys | Ile | Asn | Ser | Leu | Leu | Gln | Phe | Leu | Phe | Gly | Ser | Arg | Gln | |
| | | | | 85 | | | | | 90 | | | | | 95 | | |

| gat | ttt | ttg | aga | aat | ttt | aaa | act | tgg | agt | aac | aac | aat | aac | aat | cta | 336 |
|---|---|---|---|---|---|---|---|---|---|---|---|---|---|---|---|---|
| Asp | Phe | Leu | Arg | Asn | Phe | Lys | Thr | Trp | Ser | Asn | Asn | Asn | Asn | Asn | Leu | |
| | | | 100 | | | | | 105 | | | | | 110 | | | |

| tcg | att | tat | tta | tta | att | ttt | ggc | ata | gta | gta | ttt | ttt | tat | aaa | aaa | 384 |
|---|---|---|---|---|---|---|---|---|---|---|---|---|---|---|---|---|
| Ser | Ile | Tyr | Leu | Leu | Ile | Phe | Gly | Ile | Val | Val | Phe | Phe | Tyr | Lys | Lys | |
| | | 115 | | | | | 120 | | | | | 125 | | | | |

| cca | gac | cat | cta | aac | tac | att | gtt | gag | agc | gtt | agt | gaa | atg | aca | aca | 432 |
|---|---|---|---|---|---|---|---|---|---|---|---|---|---|---|---|---|
| Pro | Asp | His | Leu | Asn | Tyr | Ile | Val | Glu | Ser | Val | Ser | Glu | Met | Thr | Thr | |
| | 130 | | | | | 135 | | | | | 140 | | | | | |

| aac | ttc | aga | aat | aat | aat | agc | ctt | agc | cgt | tgg | ttg | ccc | aga | agt | aag | 480 |
|---|---|---|---|---|---|---|---|---|---|---|---|---|---|---|---|---|
| Asn | Phe | Arg | Asn | Asn | Asn | Ser | Leu | Ser | Arg | Trp | Leu | Pro | Arg | Ser | Lys | |
| 145 | | | | | 150 | | | | | 155 | | | | | 160 | |

| ttt | acc | cac | tta | gac | gaa | gag | atc | ttg | aaa | aga | ggt | ggt | ttc | att | gct | 528 |
|---|---|---|---|---|---|---|---|---|---|---|---|---|---|---|---|---|
| Phe | Thr | His | Leu | Asp | Glu | Glu | Ile | Leu | Lys | Arg | Gly | Gly | Phe | Ile | Ala | |
| | | | | 165 | | | | | 170 | | | | | 175 | | |

| ggt | tta | gtt | aat | gat | ggt | aac | act | tgt | ttt | atg | aac | tct | gtt | ttg | caa | 576 |
|---|---|---|---|---|---|---|---|---|---|---|---|---|---|---|---|---|
| Gly | Leu | Val | Asn | Asp | Gly | Asn | Thr | Cys | Phe | Met | Asn | Ser | Val | Leu | Gln | |
| | | | 180 | | | | | 185 | | | | | 190 | | | |

| tca | ttg | gca | tca | tcc | aga | gaa | tta | atg | gag | ttc | ttg | gac | aat | aat | gtc | 624 |
|---|---|---|---|---|---|---|---|---|---|---|---|---|---|---|---|---|
| Ser | Leu | Ala | Ser | Ser | Arg | Glu | Leu | Met | Glu | Phe | Leu | Asp | Asn | Asn | Val | |
| | | 195 | | | | | 200 | | | | | 205 | | | | |

| ata | agg | acc | tat | gag | gag | ata | gaa | caa | aat | gaa | cac | aat | gaa | gaa | gga | 672 |
|---|---|---|---|---|---|---|---|---|---|---|---|---|---|---|---|---|
| Ile | Arg | Thr | Tyr | Glu | Glu | Ile | Glu | Gln | Asn | Glu | His | Asn | Glu | Glu | Gly | |
| | 210 | | | | | 215 | | | | | 220 | | | | | |

| aac | ggg | caa | gaa | tct | gct | caa | gat | gaa | gcc | act | cat | aag | aaa | aac | act | 720 |
|---|---|---|---|---|---|---|---|---|---|---|---|---|---|---|---|---|
| Asn | Gly | Gln | Glu | Ser | Ala | Gln | Asp | Glu | Ala | Thr | His | Lys | Lys | Asn | Thr | |
| 225 | | | | | 230 | | | | | 235 | | | | | 240 | |

| cgt | aag | ggt | ggc | aaa | gtt | tat | ggt | aag | cat | aag | aag | aaa | ttg | aat | agg | 768 |
|---|---|---|---|---|---|---|---|---|---|---|---|---|---|---|---|---|
| Arg | Lys | Gly | Gly | Lys | Val | Tyr | Gly | Lys | His | Lys | Lys | Lys | Leu | Asn | Arg | |

-continued

| | | |
|---|---|---|
| aag tca agt tcg aaa gaa gac gaa gaa aag agc cag gag cca gat atc<br>Lys Ser Ser Ser Lys Glu Asp Glu Glu Lys Ser Gln Glu Pro Asp Ile<br>245                260                265                270 | 816 |
| act ttc agt gtc gcc tta agg gat cta ctt tct gcc tta aat gcg aag<br>Thr Phe Ser Val Ala Leu Arg Asp Leu Leu Ser Ala Leu Asn Ala Lys<br>           275                        280                285 | 864 |
| tat tat cgg gat aaa ccc tat ttc aaa acc aat agt tta ttg aaa gca<br>Tyr Tyr Arg Asp Lys Pro Tyr Phe Lys Thr Asn Ser Leu Leu Lys Ala<br>290                            295                      300 | 912 |
| atg tcc aaa tct cca aga aaa aat att ctt ctt ggc tac gac caa gag<br>Met Ser Lys Ser Pro Arg Lys Asn Ile Leu Leu Gly Tyr Asp Gln Glu<br>305                310                315                320 | 960 |
| gac gcg caa gaa ttc ttc cag aac ata cta gcc gag ttg gaa agt aac<br>Asp Ala Gln Glu Phe Phe Gln Asn Ile Leu Ala Glu Leu Glu Ser Asn<br>                      325                      330                335 | 1008 |
| gtt aaa tca ttg aat act gaa aaa cta gat acc act cca gtt gcg aaa<br>Val Lys Ser Leu Asn Thr Glu Lys Leu Asp Thr Thr Pro Val Ala Lys<br>           340                        345                350 | 1056 |
| tca gaa tta ccc gat gat gct tta gta ggt caa ctt aac ctt ggt gaa<br>Ser Glu Leu Pro Asp Asp Ala Leu Val Gly Gln Leu Asn Leu Gly Glu<br>355                          360                      365 | 1104 |
| gtt ggc act gtt tac att cca act gaa cag att gat cct aac tct ata<br>Val Gly Thr Val Tyr Ile Pro Thr Glu Gln Ile Asp Pro Asn Ser Ile<br>370                          375                      380 | 1152 |
| cta cat gac aag tcc att caa aat ttc aca cct ttc aaa cta atg act<br>Leu His Asp Lys Ser Ile Gln Asn Phe Thr Pro Phe Lys Leu Met Thr<br>385                390                395                400 | 1200 |
| cct tta gat ggt atc acg gca gaa aga att ggt tgt tta cag tgt ggt<br>Pro Leu Asp Gly Ile Thr Ala Glu Arg Ile Gly Cys Leu Gln Cys Gly<br>                          405                      410                415 | 1248 |
| gag aac ggt ggc ata aga tat tcc gta ttt tcg gga tta agc tta aat<br>Glu Asn Gly Gly Ile Arg Tyr Ser Val Phe Ser Gly Leu Ser Leu Asn<br>                    420                      425                430 | 1296 |
| tta ccg aac gag aat att ggt tcc act tta aaa tta tct cag tta tta<br>Leu Pro Asn Glu Asn Ile Gly Ser Thr Leu Lys Leu Ser Gln Leu Leu<br>           435                        440                445 | 1344 |
| agc gac tgg agt aaa cct gaa atc atc gaa ggc gta gaa tgt aac cgt<br>Ser Asp Trp Ser Lys Pro Glu Ile Ile Glu Gly Val Glu Cys Asn Arg<br>450                            455                      460 | 1392 |
| tgt gcc ctc aca gca gcg cac tct cat tta ttt ggt cag ttg aaa gaa<br>Cys Ala Leu Thr Ala Ala His Ser His Leu Phe Gly Gln Leu Lys Glu<br>465                470                475                480 | 1440 |
| ttt gaa aaa aaa cct gag ggt tcg atc cca gaa aag tta att aac gct<br>Phe Glu Lys Lys Pro Glu Gly Ser Ile Pro Glu Lys Leu Ile Asn Ala<br>                          485                      490                495 | 1488 |
| gta aaa gat agg gtc cat caa atc gaa gaa gtt ctt gcc aaa cca gtt<br>Val Lys Asp Arg Val His Gln Ile Glu Glu Val Leu Ala Lys Pro Val<br>           500                        505                510 | 1536 |
| att gac gat gaa gat tat aag aag ttg cat aca gca aat atg gta cgt<br>Ile Asp Asp Glu Asp Tyr Lys Lys Leu His Thr Ala Asn Met Val Arg<br>515                            520                      525 | 1584 |
| aaa tgc tct aaa tct aag cag att tta ata tca aga cct cca cca tta<br>Lys Cys Ser Lys Ser Lys Gln Ile Leu Ile Ser Arg Pro Pro Pro Leu<br>           530                        535                540 | 1632 |
| tta tcc att cat atc aac aga tcc gta ttt gat cca aga acg tac atg<br>Leu Ser Ile His Ile Asn Arg Ser Val Phe Asp Pro Arg Thr Tyr Met<br>545                550                555                560 | 1680 |
| att aga aaa aat aac tcg aaa gta ttg ttt aag tca agg ttg aat ctt | 1728 |

```
Ile Arg Lys Asn Asn Ser Lys Val Leu Phe Lys Ser Arg Leu Asn Leu
                565             570                 575 gcc cca tgg tgt tgt gat att aat gaa atc aat ttg gat gct cgt ttg    1776
Ala Pro Trp Cys Cys Asp Ile Asn Glu Ile Asn Leu Asp Ala Arg Leu
        580                 585                 590 cca atg tca aaa aag gaa aaa gct gcg caa caa gat tca agt gaa gat    1824
Pro Met Ser Lys Lys Glu Lys Ala Ala Gln Gln Asp Ser Ser Glu Asp
            595                 600                 605 gaa aac att ggc ggt gaa tac tat acg aaa tta cat gaa cgc ttc gag    1872
Glu Asn Ile Gly Gly Glu Tyr Tyr Thr Lys Leu His Glu Arg Phe Glu
        610                 615                 620 cag gaa ttt gaa gac agc gag gaa gaa aaa gaa tac gat gac gca gag    1920
Gln Glu Phe Glu Asp Ser Glu Glu Glu Lys Glu Tyr Asp Asp Ala Glu
625                 630                 635                 640 ggg aac tat gcg tct cat tac aat cat acc aag gat atc agt aac tat    1968
Gly Asn Tyr Ala Ser His Tyr Asn His Thr Lys Asp Ile Ser Asn Tyr
                645                 650                 655 gat ccc cta aac ggt gaa gtc gat ggc gtg aca tcc gat gat gaa gat    2016
Asp Pro Leu Asn Gly Glu Val Asp Gly Val Thr Ser Asp Asp Glu Asp
            660                 665                 670 gag tac att gaa gaa acc gat gct tta ggg aat aca atc aaa aaa agg    2064
Glu Tyr Ile Glu Glu Thr Asp Ala Leu Gly Asn Thr Ile Lys Lys Arg
        675                 680                 685 atc ata gaa cat tct gat gtt gaa aac gag aat gta aaa gat aat gaa    2112
Ile Ile Glu His Ser Asp Val Glu Asn Glu Asn Val Lys Asp Asn Glu
    690                 695                 700 gaa ctg caa gaa atc gac aat gtg agc ctt gac gaa cca aag atc aat    2160
Glu Leu Gln Glu Ile Asp Asn Val Ser Leu Asp Glu Pro Lys Ile Asn
705                 710                 715                 720 gtt gaa gat caa cta gaa aca tca tct gat gag gaa gat gta ata cca    2208
Val Glu Asp Gln Leu Glu Thr Ser Ser Asp Glu Glu Asp Val Ile Pro
                725                 730                 735 gct cca cct atc aat tat gct agg tca ttt tcc aca gtt cca gcc act    2256
Ala Pro Pro Ile Asn Tyr Ala Arg Ser Phe Ser Thr Val Pro Ala Thr
            740                 745                 750 cca ttg aca tat tca ttg cgc tct gtc att gtt cac tac ggt acc cat    2304
Pro Leu Thr Tyr Ser Leu Arg Ser Val Ile Val His Tyr Gly Thr His
        755                 760                 765 aat tat ggt cat tac att gca ttt aga aaa tac agg ggt tgt tgg tgg    2352
Asn Tyr Gly His Tyr Ile Ala Phe Arg Lys Tyr Arg Gly Cys Trp Trp
    770                 775                 780 aga ata tct gat gag act gtg tac gtt gtg gac gaa gct gaa gtc ctt    2400
Arg Ile Ser Asp Glu Thr Val Tyr Val Val Asp Glu Ala Glu Val Leu
785                 790                 795                 800 tca aca ccc ggt gta ttt atg tta ttt tac gaa tat gac ttt gat gaa    2448
Ser Thr Pro Gly Val Phe Met Leu Phe Tyr Glu Tyr Asp Phe Asp Glu
                805                 810                 815 gaa act ggg aag atg aag gat gat ttg gaa gct att cag agt aat aat    2496
Glu Thr Gly Lys Met Lys Asp Asp Leu Glu Ala Ile Gln Ser Asn Asn
            820                 825                 830 gaa gaa gat gat gaa aaa gag cag gag caa aaa gga gtc cag gag cca    2544
Glu Glu Asp Asp Glu Lys Glu Gln Glu Gln Lys Gly Val Gln Glu Pro
        835                 840                 845 aag gaa agc caa gag caa gga gaa ggt gaa gag caa gag gaa ggt caa    2592
Lys Glu Ser Gln Glu Gln Gly Glu Gly Glu Glu Gln Glu Glu Gly Gln
    850                 855                 860 gag cag atg aag ttc gag aga aca gaa gac cat aga gat att tct ggt    2640
Glu Gln Met Lys Phe Glu Arg Thr Glu Asp His Arg Asp Ile Ser Gly
865                 870                 875                 880
```

```
aaa gat gta aac taa                                              2655
Lys Asp Val Asn
```

<210> SEQ ID NO 2
<211> LENGTH: 884
<212> TYPE: PRT
<213> ORGANISM: artificial sequence
<220> FEATURE:
<223> OTHER INFORMATION: Synthetic Construct

<400> SEQUENCE: 2

```
Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ser Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Asp Leu Phe Ile
65                  70                  75                  80

Glu Ser Lys Ile Asn Ser Leu Leu Gln Phe Leu Phe Gly Ser Arg Gln
                85                  90                  95

Asp Phe Leu Arg Asn Phe Lys Thr Trp Ser Asn Asn Asn Asn Asn Leu
            100                 105                 110

Ser Ile Tyr Leu Leu Ile Phe Gly Ile Val Val Phe Phe Tyr Lys Lys
        115                 120                 125

Pro Asp His Leu Asn Tyr Ile Val Glu Ser Val Ser Glu Met Thr Thr
    130                 135                 140

Asn Phe Arg Asn Asn Ser Leu Ser Arg Trp Leu Pro Arg Ser Lys
145                 150                 155                 160

Phe Thr His Leu Asp Glu Glu Ile Leu Lys Arg Gly Gly Phe Ile Ala
                165                 170                 175

Gly Leu Val Asn Asp Gly Asn Thr Cys Phe Met Asn Ser Val Leu Gln
            180                 185                 190

Ser Leu Ala Ser Ser Arg Glu Leu Met Glu Phe Leu Asp Asn Asn Val
        195                 200                 205

Ile Arg Thr Tyr Glu Glu Ile Glu Gln Asn Glu His Asn Glu Glu Gly
    210                 215                 220

Asn Gly Gln Glu Ser Ala Gln Asp Glu Ala Thr His Lys Lys Asn Thr
225                 230                 235                 240

Arg Lys Gly Gly Lys Val Tyr Gly Lys His Lys Lys Leu Asn Arg
                245                 250                 255

Lys Ser Ser Lys Glu Asp Glu Lys Ser Gln Glu Pro Asp Ile
            260                 265                 270

Thr Phe Ser Val Ala Leu Arg Asp Leu Leu Ser Ala Leu Asn Ala Lys
        275                 280                 285

Tyr Tyr Arg Asp Lys Pro Tyr Phe Lys Thr Asn Ser Leu Leu Lys Ala
    290                 295                 300

Met Ser Lys Ser Pro Arg Lys Asn Ile Leu Leu Gly Tyr Asp Gln Glu
305                 310                 315                 320

Asp Ala Gln Glu Phe Phe Gln Asn Ile Leu Ala Glu Leu Glu Ser Asn
                325                 330                 335

Val Lys Ser Leu Asn Thr Glu Lys Leu Asp Thr Thr Pro Val Ala Lys
            340                 345                 350
```

-continued

```
Ser Glu Leu Pro Asp Asp Ala Leu Val Gly Gln Leu Asn Leu Gly Glu
            355                 360                 365
Val Gly Thr Val Tyr Ile Pro Thr Glu Gln Ile Asp Pro Asn Ser Ile
        370                 375                 380
Leu His Asp Lys Ser Ile Gln Asn Phe Thr Pro Phe Lys Leu Met Thr
385                 390                 395                 400
Pro Leu Asp Gly Ile Thr Ala Glu Arg Ile Gly Cys Leu Gln Cys Gly
                405                 410                 415
Glu Asn Gly Gly Ile Arg Tyr Ser Val Phe Ser Gly Leu Ser Leu Asn
            420                 425                 430
Leu Pro Asn Glu Asn Ile Gly Ser Thr Leu Lys Leu Ser Gln Leu Leu
        435                 440                 445
Ser Asp Trp Ser Lys Pro Glu Ile Ile Glu Gly Val Glu Cys Asn Arg
450                 455                 460
Cys Ala Leu Thr Ala Ala His Ser His Leu Phe Gly Gln Leu Lys Glu
465                 470                 475                 480
Phe Glu Lys Lys Pro Glu Gly Ser Ile Pro Gly Lys Leu Ile Asn Ala
                485                 490                 495
Val Lys Asp Arg Val His Gln Ile Glu Glu Val Leu Ala Lys Pro Val
            500                 505                 510
Ile Asp Asp Glu Asp Tyr Lys Lys Leu His Thr Ala Asn Met Val Arg
        515                 520                 525
Lys Cys Ser Lys Ser Lys Gln Ile Leu Ile Ser Arg Pro Pro Pro Leu
530                 535                 540
Leu Ser Ile His Ile Asn Arg Ser Val Phe Asp Pro Arg Thr Tyr Met
545                 550                 555                 560
Ile Arg Lys Asn Asn Ser Lys Val Leu Phe Lys Ser Arg Leu Asn Leu
                565                 570                 575
Ala Pro Trp Cys Cys Asp Ile Asn Glu Ile Asn Leu Asp Ala Arg Leu
            580                 585                 590
Pro Met Ser Lys Lys Glu Lys Ala Ala Gln Gln Asp Ser Ser Glu Asp
        595                 600                 605
Glu Asn Ile Gly Gly Glu Tyr Tyr Thr Lys Leu His Glu Arg Phe Glu
610                 615                 620
Gln Glu Phe Glu Asp Ser Glu Glu Lys Glu Tyr Asp Asp Ala Glu
625                 630                 635                 640
Gly Asn Tyr Ala Ser His Tyr Asn His Thr Lys Asp Ile Ser Asn Tyr
                645                 650                 655
Asp Pro Leu Asn Gly Glu Val Asp Gly Val Thr Ser Asp Glu Asp
            660                 665                 670
Glu Tyr Ile Glu Glu Thr Asp Ala Leu Gly Asn Thr Ile Lys Lys Arg
        675                 680                 685
Ile Ile Glu His Ser Asp Val Glu Asn Glu Asn Val Lys Asp Asn Glu
690                 695                 700
Glu Leu Gln Glu Ile Asp Asn Val Ser Leu Asp Glu Pro Lys Ile Asn
705                 710                 715                 720
Val Glu Asp Gln Leu Glu Thr Ser Ser Asp Glu Glu Asp Val Ile Pro
                725                 730                 735
Ala Pro Pro Ile Asn Tyr Ala Arg Ser Phe Ser Thr Val Pro Ala Thr
            740                 745                 750
Pro Leu Thr Tyr Ser Leu Arg Ser Val Ile Val His Tyr Gly Thr His
        755                 760                 765
Asn Tyr Gly His Tyr Ile Ala Phe Arg Lys Tyr Arg Gly Cys Trp Trp
```

```
                770               775               780
Arg Ile Ser Asp Glu Thr Val Tyr Val Val Asp Glu Ala Glu Val Leu
785                 790                 795                 800

Ser Thr Pro Gly Val Phe Met Leu Phe Tyr Glu Tyr Asp Phe Asp Glu
                805                 810                 815

Glu Thr Gly Lys Met Lys Asp Asp Leu Glu Ala Ile Gln Ser Asn Asn
                820                 825                 830

Glu Glu Asp Asp Glu Lys Glu Gln Glu Gln Lys Gly Val Gln Glu Pro
                835                 840                 845

Lys Glu Ser Gln Glu Gln Gly Glu Gly Glu Gln Glu Gly Gln
    850                 855                 860

Glu Gln Met Lys Phe Glu Arg Thr Glu Asp His Arg Asp Ile Ser Gly
865                 870                 875                 880

Lys Asp Val Asn

<210> SEQ ID NO 3
<211> LENGTH: 2496
<212> TYPE: DNA
<213> ORGANISM: artificial sequence
<220> FEATURE:
<223> OTHER INFORMATION: UBI::UBP1deltaC
<220> FEATURE:
<221> NAME/KEY: CDS
<222> LOCATION: (1)..(2496)
<223> OTHER INFORMATION: sequence coding the hybrid protein UBI::
      UBP1deltaC with the transmembrane domain removed

<400> SEQUENCE: 3 atg cag att ttc gtc aaa act ttg acc ggt aaa acc ata aca ttg gaa      48
Met Gln Ile Phe Val Lys Thr Leu Thr Gly Lys Thr Ile Thr Leu Glu
1               5                   10                  15 gtt gaa tct tcc gat acc atc gac aac gtt aag tcg aaa att caa gac      96
Val Glu Ser Ser Asp Thr Ile Asp Asn Val Lys Ser Lys Ile Gln Asp
            20                  25                  30 aag gaa ggt atc cct cca gat caa caa aga ttg atc ttt gcc ggt aag     144
Lys Glu Gly Ile Pro Pro Asp Gln Gln Arg Leu Ile Phe Ala Gly Lys
        35                  40                  45 cag cta gaa gac ggt aga acg ctg tct gat tac aac att cag aag gag     192
Gln Leu Glu Asp Gly Arg Thr Leu Ser Asp Tyr Asn Ile Gln Lys Glu
    50                  55                  60 tcc acc tta cat ctt gtc tta aga ctc cgc ggt ggt gac cat cta aac     240
Ser Thr Leu His Leu Val Leu Arg Leu Arg Gly Gly Asp His Leu Asn
65                  70                  75                  80 tac att gtt gag agc gtt agt gaa atg aca aca aac ttc aga aat aat     288
Tyr Ile Val Glu Ser Val Ser Glu Met Thr Thr Asn Phe Arg Asn Asn
                85                  90                  95 aat agc ctt agc cgt tgg ttg ccc aga agt aag ttt acc cac tta gac     336
Asn Ser Leu Ser Arg Trp Leu Pro Arg Ser Lys Phe Thr His Leu Asp
            100                 105                 110 gaa gag atc ttg aaa aga ggt ggt ttc att gct ggt tta gtt aat gat     384
Glu Glu Ile Leu Lys Arg Gly Gly Phe Ile Ala Gly Leu Val Asn Asp
        115                 120                 125 ggt aac act tgt ttt atg aac tct gtt ttg caa tca ttg gca tca tcc     432
Gly Asn Thr Cys Phe Met Asn Ser Val Leu Gln Ser Leu Ala Ser Ser
    130                 135                 140 aga gaa tta atg gag ttc ttg gac aat aat gtc ata agg acc tat gag     480
Arg Glu Leu Met Glu Phe Leu Asp Asn Asn Val Ile Arg Thr Tyr Glu
145                 150                 155                 160 gag ata gaa caa aat gaa cac aat gaa gaa gga aac ggg caa gaa tct     528
Glu Ile Glu Gln Asn Glu His Asn Glu Glu Gly Asn Gly Gln Glu Ser
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 165 |     |     |     |     | 170 |     |     |     |     | 175 |     |      |
| gct | caa | gat | gaa | gcc | act | cat | aag | aaa | aac | act | cgt | aag | ggt | ggc | aaa | 576  |
| Ala | Gln | Asp | Glu | Ala | Thr | His | Lys | Lys | Asn | Thr | Arg | Lys | Gly | Gly | Lys |      |
|     |     |     | 180 |     |     |     |     | 185 |     |     |     |     | 190 |     |     |      |
| gtt | tat | ggt | aag | cat | aag | aag | aaa | ttg | aat | agg | aag | tca | agt | tcg | aaa | 624  |
| Val | Tyr | Gly | Lys | His | Lys | Lys | Lys | Leu | Asn | Arg | Lys | Ser | Ser | Ser | Lys |      |
|     |     | 195 |     |     |     |     | 200 |     |     |     |     | 205 |     |     |     |      |
| gaa | gac | gaa | gaa | aag | agc | cag | gag | cca | gat | atc | act | ttc | agt | gtc | gcc | 672  |
| Glu | Asp | Glu | Glu | Lys | Ser | Gln | Glu | Pro | Asp | Ile | Thr | Phe | Ser | Val | Ala |      |
|     | 210 |     |     |     |     | 215 |     |     |     |     | 220 |     |     |     |     |      |
| tta | agg | gat | cta | ctt | tct | gcc | tta | aat | gcg | aag | tat | tat | cgg | gat | aaa | 720  |
| Leu | Arg | Asp | Leu | Leu | Ser | Ala | Leu | Asn | Ala | Lys | Tyr | Tyr | Arg | Asp | Lys |      |
| 225 |     |     |     |     | 230 |     |     |     |     | 235 |     |     |     |     | 240 |      |
| ccc | tat | ttc | aaa | acc | aat | agt | tta | ttg | aaa | gca | atg | tcc | aaa | tct | cca | 768  |
| Pro | Tyr | Phe | Lys | Thr | Asn | Ser | Leu | Leu | Lys | Ala | Met | Ser | Lys | Ser | Pro |      |
|     |     |     |     | 245 |     |     |     |     | 250 |     |     |     |     | 255 |     |      |
| aga | aaa | aat | att | ctt | ctt | ggc | tac | gac | caa | gag | gac | gcg | caa | gaa | ttc | 816  |
| Arg | Lys | Asn | Ile | Leu | Leu | Gly | Tyr | Asp | Gln | Glu | Asp | Ala | Gln | Glu | Phe |      |
|     |     |     | 260 |     |     |     |     | 265 |     |     |     |     | 270 |     |     |      |
| ttc | cag | aac | ata | cta | gcc | gag | ttg | gaa | agt | aac | gtt | aaa | tca | ttg | aat | 864  |
| Phe | Gln | Asn | Ile | Leu | Ala | Glu | Leu | Glu | Ser | Asn | Val | Lys | Ser | Leu | Asn |      |
|     |     | 275 |     |     |     |     | 280 |     |     |     |     | 285 |     |     |     |      |
| act | gaa | aaa | cta | gat | acc | act | cca | gtt | gcg | aaa | tca | gaa | tta | ccc | gat | 912  |
| Thr | Glu | Lys | Leu | Asp | Thr | Thr | Pro | Val | Ala | Lys | Ser | Glu | Leu | Pro | Asp |      |
|     | 290 |     |     |     |     | 295 |     |     |     |     | 300 |     |     |     |     |      |
| gat | gct | tta | gta | ggt | caa | ctt | aac | ctt | ggt | gaa | gtt | ggc | act | gtt | tac | 960  |
| Asp | Ala | Leu | Val | Gly | Gln | Leu | Asn | Leu | Gly | Glu | Val | Gly | Thr | Val | Tyr |      |
| 305 |     |     |     |     | 310 |     |     |     |     | 315 |     |     |     |     | 320 |      |
| att | cca | act | gaa | cag | att | gat | cct | aac | tct | ata | cta | cat | gac | aag | tcc | 1008 |
| Ile | Pro | Thr | Glu | Gln | Ile | Asp | Pro | Asn | Ser | Ile | Leu | His | Asp | Lys | Ser |      |
|     |     |     |     | 325 |     |     |     |     | 330 |     |     |     |     | 335 |     |      |
| att | caa | aat | ttc | aca | cct | ttc | aaa | cta | atg | act | cct | tta | gat | ggt | atc | 1056 |
| Ile | Gln | Asn | Phe | Thr | Pro | Phe | Lys | Leu | Met | Thr | Pro | Leu | Asp | Gly | Ile |      |
|     |     |     | 340 |     |     |     |     | 345 |     |     |     |     | 350 |     |     |      |
| acg | gca | gaa | aga | att | ggt | tgt | tta | cag | tgt | ggt | gag | aac | ggt | ggc | ata | 1104 |
| Thr | Ala | Glu | Arg | Ile | Gly | Cys | Leu | Gln | Cys | Gly | Glu | Asn | Gly | Gly | Ile |      |
|     |     | 355 |     |     |     |     | 360 |     |     |     |     | 365 |     |     |     |      |
| aga | tat | tcc | gta | ttt | tcg | gga | tta | agc | tta | aat | tta | ccg | aac | gag | aat | 1152 |
| Arg | Tyr | Ser | Val | Phe | Ser | Gly | Leu | Ser | Leu | Asn | Leu | Pro | Asn | Glu | Asn |      |
|     | 370 |     |     |     |     | 375 |     |     |     |     | 380 |     |     |     |     |      |
| att | ggt | tcc | act | tta | aaa | tta | tct | cag | tta | tta | agc | gac | tgg | agt | aaa | 1200 |
| Ile | Gly | Ser | Thr | Leu | Lys | Leu | Ser | Gln | Leu | Leu | Ser | Asp | Trp | Ser | Lys |      |
| 385 |     |     |     |     | 390 |     |     |     |     | 395 |     |     |     |     | 400 |      |
| cct | gaa | atc | atc | gaa | ggc | gta | gaa | tgt | aac | cgt | tgt | gcc | ctc | aca | gca | 1248 |
| Pro | Glu | Ile | Ile | Glu | Gly | Val | Glu | Cys | Asn | Arg | Cys | Ala | Leu | Thr | Ala |      |
|     |     |     |     | 405 |     |     |     |     | 410 |     |     |     |     | 415 |     |      |
| gcg | cac | tct | cat | tta | ttt | ggt | cag | ttg | aaa | gaa | ttt | gaa | aaa | aaa | cct | 1296 |
| Ala | His | Ser | His | Leu | Phe | Gly | Gln | Leu | Lys | Glu | Phe | Glu | Lys | Lys | Pro |      |
|     |     |     | 420 |     |     |     |     | 425 |     |     |     |     | 430 |     |     |      |
| gag | ggt | tcg | atc | cca | gaa | aag | tta | att | aac | gct | gta | aaa | gat | agg | gtc | 1344 |
| Glu | Gly | Ser | Ile | Pro | Glu | Lys | Leu | Ile | Asn | Ala | Val | Lys | Asp | Arg | Val |      |
|     |     | 435 |     |     |     |     | 440 |     |     |     |     | 445 |     |     |     |      |
| cat | caa | atc | gaa | gaa | gtt | ctt | gcc | aaa | cca | gtt | att | gac | gat | gaa | gat | 1392 |
| His | Gln | Ile | Glu | Glu | Val | Leu | Ala | Lys | Pro | Val | Ile | Asp | Asp | Glu | Asp |      |
|     | 450 |     |     |     |     | 455 |     |     |     |     | 460 |     |     |     |     |      |
| tat | aag | aag | ttg | cat | aca | gca | aat | atg | gta | cgt | aaa | tgc | tct | aaa | tct | 1440 |
| Tyr | Lys | Lys | Leu | His | Thr | Ala | Asn | Met | Val | Arg | Lys | Cys | Ser | Lys | Ser |      |
| 465 |     |     |     |     | 470 |     |     |     |     | 475 |     |     |     |     | 480 |      |
| aag | cag | att | tta | ata | tca | aga | cct | cca | cca | tta | tta | tcc | att | cat | atc | 1488 |

|  |  |  |  |  |  |  |  |  |  |  |  |  |  |  |  |
|---|---|---|---|---|---|---|---|---|---|---|---|---|---|---|---|
| Lys | Gln | Ile | Leu | Ile | Ser | Arg | Pro | Pro | Leu | Leu | Ser | Ile | His | Ile |  |
|  |  |  |  | 485 |  |  |  | 490 |  |  |  |  | 495 |  |  |

```
aac aga tcc gta ttt gat cca aga acg tac atg att aga aaa aat aac      1536
Asn Arg Ser Val Phe Asp Pro Arg Thr Tyr Met Ile Arg Lys Asn Asn
            500                 505                 510 tcg aaa gta ttg ttt aag tca agg ttg aat ctt gcc cca tgg tgt tgt      1584
Ser Lys Val Leu Phe Lys Ser Arg Leu Asn Leu Ala Pro Trp Cys Cys
        515                 520                 525 gat att aat gaa atc aat ttg gat gct cgt ttg cca atg tca aaa aag      1632
Asp Ile Asn Glu Ile Asn Leu Asp Ala Arg Leu Pro Met Ser Lys Lys
530                 535                 540 gaa aaa gct gcg caa caa gat tca agt gaa gat gaa aac att ggc ggt      1680
Glu Lys Ala Ala Gln Gln Asp Ser Ser Glu Asp Glu Asn Ile Gly Gly
545                 550                 555                 560 gaa tac tat acg aaa tta cat gaa cgc ttc gag cag gaa ttt gaa gac      1728
Glu Tyr Tyr Thr Lys Leu His Glu Arg Phe Glu Gln Glu Phe Glu Asp
                565                 570                 575 agc gag gaa gaa aaa gaa tac gat gac gca gag ggg aac tat gcg tct      1776
Ser Glu Glu Glu Lys Glu Tyr Asp Asp Ala Glu Gly Asn Tyr Ala Ser
            580                 585                 590 cat tac aat cat acc aag gat atc agt aac tat gat ccc cta aac ggt      1824
His Tyr Asn His Thr Lys Asp Ile Ser Asn Tyr Asp Pro Leu Asn Gly
        595                 600                 605 gaa gtc gat ggc gtg aca tcc gat gat gaa gat gag tac att gaa gaa      1872
Glu Val Asp Gly Val Thr Ser Asp Asp Glu Asp Glu Tyr Ile Glu Glu
610                 615                 620 acc gat gct tta ggg aat aca atc aaa aaa agg atc ata gaa cat tct      1920
Thr Asp Ala Leu Gly Asn Thr Ile Lys Lys Arg Ile Ile Glu His Ser
625                 630                 635                 640 gat gtt gaa aac gag aat gta aaa gat aat gaa gaa ctg caa gaa atc      1968
Asp Val Glu Asn Glu Asn Val Lys Asp Asn Glu Glu Leu Gln Glu Ile
                645                 650                 655 gac aat gtg agc ctt gac gaa cca aag atc aat gtt gaa gat caa cta      2016
Asp Asn Val Ser Leu Asp Glu Pro Lys Ile Asn Val Glu Asp Gln Leu
            660                 665                 670 gaa aca tca tct gat gag gaa gat gtt ata cca gct cca cct atc aat      2064
Glu Thr Ser Ser Asp Glu Glu Asp Val Ile Pro Ala Pro Pro Ile Asn
        675                 680                 685 tat gct agg tca ttt tcc aca gtt cca gcc act cca ttg aca tat tca      2112
Tyr Ala Arg Ser Phe Ser Thr Val Pro Ala Thr Pro Leu Thr Tyr Ser
690                 695                 700 ttg cgc tct gtc att gtt cac tac ggt acc cat aat tat ggt cat tac      2160
Leu Arg Ser Val Ile Val His Tyr Gly Thr His Asn Tyr Gly His Tyr
705                 710                 715                 720 att gca ttt aga aaa tac agg ggt tgt tgg tgg aga ata tct gat gag      2208
Ile Ala Phe Arg Lys Tyr Arg Gly Cys Trp Trp Arg Ile Ser Asp Glu
                725                 730                 735 act gtg tac gtt gtg gac gaa gct gaa gtc ctt tca aca ccc ggt gta      2256
Thr Val Tyr Val Val Asp Glu Ala Glu Val Leu Ser Thr Pro Gly Val
            740                 745                 750 ttt atg tta ttt tac gaa tat gac ttt gat gaa gaa act ggg aag atg      2304
Phe Met Leu Phe Tyr Glu Tyr Asp Phe Asp Glu Glu Thr Gly Lys Met
        755                 760                 765 aag gat gat ttg gaa gct att cag agt aat aat gaa gaa gat gat gaa      2352
Lys Asp Asp Leu Glu Ala Ile Gln Ser Asn Asn Glu Glu Asp Asp Glu
770                 775                 780 aaa gag cag gag caa aaa gga gtc cag gag cca aag gaa agc caa gag      2400
Lys Glu Gln Glu Gln Lys Gly Val Gln Glu Pro Lys Glu Ser Gln Glu
785                 790                 795                 800
```

-continued

```
caa gga gaa ggt gaa gag caa gag gaa ggt caa gag cag atg aag ttc    2448
Gln Gly Glu Gly Glu Glu Gln Glu Glu Gly Gln Glu Gln Met Lys Phe
                805                 810                 815 gag aga aca gaa gac cat aga gat att tct ggt aaa gat gta aac taa    2496
Glu Arg Thr Glu Asp His Arg Asp Ile Ser Gly Lys Asp Val Asn
        820                 825                 830
```

<210> SEQ ID NO 4
<211> LENGTH: 831
<212> TYPE: PRT
<213> ORGANISM: artificial sequence
<220> FEATURE:
<223> OTHER INFORMATION: Synthetic Construct

<400> SEQUENCE: 4

```
Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ser Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Asp His Leu Asn
65                  70                  75                  80

Tyr Ile Val Glu Ser Val Ser Glu Met Thr Thr Asn Phe Arg Asn Asn
                85                  90                  95

Asn Ser Leu Ser Arg Trp Leu Pro Arg Ser Lys Phe Thr His Leu Asp
            100                 105                 110

Glu Glu Ile Leu Lys Arg Gly Gly Phe Ile Ala Gly Leu Val Asn Asp
        115                 120                 125

Gly Asn Thr Cys Phe Met Asn Ser Val Leu Gln Ser Leu Ala Ser Ser
    130                 135                 140

Arg Glu Leu Met Glu Phe Leu Asp Asn Asn Val Ile Arg Thr Tyr Glu
145                 150                 155                 160

Glu Ile Glu Gln Asn Glu His Asn Glu Glu Gly Asn Gly Gln Glu Ser
                165                 170                 175

Ala Gln Asp Glu Ala Thr His Lys Lys Asn Thr Arg Lys Gly Gly Lys
            180                 185                 190

Val Tyr Gly Lys His Lys Lys Leu Asn Arg Lys Ser Ser Ser Lys
        195                 200                 205

Glu Asp Glu Glu Lys Ser Gln Glu Pro Asp Ile Thr Phe Ser Val Ala
    210                 215                 220

Leu Arg Asp Leu Leu Ser Ala Leu Asn Ala Lys Tyr Tyr Arg Asp Lys
225                 230                 235                 240

Pro Tyr Phe Lys Thr Asn Ser Leu Leu Lys Ala Met Ser Lys Ser Pro
                245                 250                 255

Arg Lys Asn Ile Leu Leu Gly Tyr Asp Gln Glu Asp Ala Gln Glu Phe
            260                 265                 270

Phe Gln Asn Ile Leu Ala Glu Leu Glu Ser Asn Val Lys Ser Leu Asn
        275                 280                 285

Thr Glu Lys Leu Asp Thr Thr Pro Val Ala Lys Ser Glu Leu Pro Asp
    290                 295                 300

Asp Ala Leu Val Gly Gln Leu Asn Leu Gly Glu Val Gly Thr Val Tyr
305                 310                 315                 320

Ile Pro Thr Glu Gln Ile Asp Pro Asn Ser Ile Leu His Asp Lys Ser
```

```
                    325                 330                 335
Ile Gln Asn Phe Thr Pro Phe Lys Leu Met Thr Pro Leu Asp Gly Ile
            340                 345                 350
Thr Ala Glu Arg Ile Gly Cys Leu Gln Cys Gly Glu Asn Gly Gly Ile
            355                 360                 365
Arg Tyr Ser Val Phe Ser Gly Leu Ser Leu Asn Leu Pro Asn Glu Asn
            370                 375                 380
Ile Gly Ser Thr Leu Lys Leu Ser Gln Leu Leu Ser Asp Trp Ser Lys
385                 390                 395                 400
Pro Glu Ile Ile Glu Gly Val Glu Cys Asn Arg Cys Ala Leu Thr Ala
                    405                 410                 415
Ala His Ser His Leu Phe Gly Gln Leu Lys Glu Phe Glu Lys Lys Pro
            420                 425                 430
Glu Gly Ser Ile Pro Glu Lys Leu Ile Asn Ala Val Lys Asp Arg Val
            435                 440                 445
His Gln Ile Glu Glu Val Leu Ala Lys Pro Val Ile Asp Asp Glu Asp
        450                 455                 460
Tyr Lys Lys Leu His Thr Ala Asn Met Val Arg Lys Cys Ser Lys Ser
465                 470                 475                 480
Lys Gln Ile Leu Ile Ser Arg Pro Pro Leu Leu Ser Ile His Ile
            485                 490                 495
Asn Arg Ser Val Phe Asp Pro Arg Thr Tyr Met Ile Arg Lys Asn Asn
            500                 505                 510
Ser Lys Val Leu Phe Lys Ser Arg Leu Asn Leu Ala Pro Trp Cys Cys
            515                 520                 525
Asp Ile Asn Glu Ile Asn Leu Asp Ala Arg Leu Pro Met Ser Lys Lys
        530                 535                 540
Glu Lys Ala Ala Gln Asp Ser Ser Glu Asp Glu Asn Ile Gly Gly
545                 550                 555                 560
Glu Tyr Tyr Thr Lys Leu His Glu Arg Phe Glu Gln Glu Phe Glu Asp
                    565                 570                 575
Ser Glu Glu Glu Lys Glu Tyr Asp Asp Ala Glu Gly Asn Tyr Ala Ser
            580                 585                 590
His Tyr Asn His Thr Lys Asp Ile Ser Asn Tyr Asp Pro Leu Asn Gly
            595                 600                 605
Glu Val Asp Gly Val Thr Ser Asp Glu Asp Glu Tyr Ile Glu Glu
            610                 615                 620
Thr Asp Ala Leu Gly Asn Thr Ile Lys Lys Arg Ile Ile Glu His Ser
625                 630                 635                 640
Asp Val Glu Asn Glu Asn Val Lys Asp Asn Glu Glu Leu Gln Glu Ile
                    645                 650                 655
Asp Asn Val Ser Leu Asp Glu Pro Lys Ile Asn Val Glu Asp Gln Leu
            660                 665                 670
Glu Thr Ser Ser Asp Glu Glu Asp Val Ile Pro Ala Pro Pro Ile Asn
            675                 680                 685
Tyr Ala Arg Ser Phe Ser Thr Val Pro Ala Thr Pro Leu Thr Tyr Ser
            690                 695                 700
Leu Arg Ser Val Ile Val His Tyr Gly Thr His Asn Tyr Gly His Tyr
705                 710                 715                 720
Ile Ala Phe Arg Lys Tyr Arg Gly Cys Trp Trp Arg Ile Ser Asp Glu
                    725                 730                 735
Thr Val Tyr Val Val Asp Glu Ala Glu Val Leu Ser Thr Pro Gly Val
            740                 745                 750
```

```
Phe Met Leu Phe Tyr Glu Tyr Asp Phe Asp Glu Glu Thr Gly Lys Met
        755                 760                 765

Lys Asp Asp Leu Glu Ala Ile Gln Ser Asn Asn Glu Asp Asp Glu
770                 775                 780

Lys Glu Gln Glu Gln Lys Gly Val Gln Glu Pro Lys Glu Ser Gln Glu
785                 790                 795                 800

Gln Gly Glu Gly Glu Glu Glu Glu Gly Gln Glu Gln Met Lys Phe
                805                 810                 815

Glu Arg Thr Glu Asp His Arg Asp Ile Ser Gly Lys Asp Val Asn
                820                 825                 830

<210> SEQ ID NO 5
<211> LENGTH: 809
<212> TYPE: PRT
<213> ORGANISM: Saccharomyces cerevisiae

<400> SEQUENCE: 5

Met Asp Leu Phe Ile Glu Ser Lys Ile Asn Ser Leu Leu Gln Phe Leu
1               5                   10                  15

Phe Gly Ser Arg Gln Asp Phe Leu Arg Asn Phe Lys Thr Trp Ser Asn
            20                  25                  30

Asn Asn Asn Asn Leu Ser Ile Tyr Leu Leu Ile Phe Gly Ile Val Val
        35                  40                  45

Phe Phe Tyr Lys Lys Pro Asp His Leu Asn Tyr Ile Val Glu Ser Val
    50                  55                  60

Ser Glu Met Thr Thr Asn Phe Arg Asn Asn Asn Ser Leu Ser Arg Trp
65                  70                  75                  80

Leu Pro Arg Ser Lys Phe Thr His Leu Asp Glu Glu Ile Leu Lys Arg
                85                  90                  95

Gly Gly Phe Ile Ala Gly Leu Val Asn Asp Gly Asn Thr Cys Phe Met
            100                 105                 110

Asn Ser Val Leu Gln Ser Leu Ala Ser Ser Arg Glu Leu Met Glu Phe
        115                 120                 125

Leu Asp Asn Asn Val Ile Arg Thr Tyr Glu Glu Ile Glu Gln Asn Glu
    130                 135                 140

His Asn Glu Glu Gly Asn Gly Gln Glu Ser Ala Gln Asp Glu Ala Thr
145                 150                 155                 160

His Lys Lys Asn Thr Arg Lys Gly Gly Lys Val Tyr Gly Lys His Lys
                165                 170                 175

Lys Lys Leu Asn Arg Lys Ser Ser Lys Glu Asp Gly Glu Lys Ser
            180                 185                 190

Gln Glu Pro Asp Ile Thr Phe Ser Val Ala Leu Arg Asp Leu Leu Ser
    195                 200                 205

Ala Leu Asn Ala Lys Tyr Tyr Arg Asp Lys Pro Tyr Phe Lys Thr Asn
210                 215                 220

Ser Leu Leu Lys Ala Met Ser Lys Ser Pro Arg Lys Asn Ile Leu Leu
225                 230                 235                 240

Gly Tyr Asp Gln Glu Asp Ala Gln Glu Phe Phe Gln Asn Ile Leu Ala
                245                 250                 255

Glu Leu Glu Ser Asn Val Lys Ser Leu Asn Thr Glu Lys Leu Asp Thr
            260                 265                 270

Thr Pro Val Ala Lys Ser Glu Leu Pro Asp Asp Ala Leu Val Gly Gln
        275                 280                 285

Leu Asn Leu Gly Glu Val Gly Thr Val Tyr Ile Pro Thr Glu Gln Ile
```

```
            290                 295                 300
Asp Pro Asn Ser Ile Leu His Asp Lys Ser Ile Gln Asn Phe Thr Pro
305                 310                 315                 320

Phe Lys Leu Met Thr Pro Leu Asp Gly Ile Thr Ala Glu Arg Ile Gly
                325                 330                 335

Cys Leu Gln Cys Gly Glu Asn Gly Gly Ile Arg Tyr Ser Val Phe Ser
                340                 345                 350

Gly Leu Ser Leu Asn Leu Pro Asn Glu Asn Ile Gly Ser Thr Leu Lys
                355                 360                 365

Leu Ser Gln Leu Leu Ser Asp Trp Ser Lys Pro Glu Ile Ile Glu Gly
                370                 375                 380

Val Glu Cys Asn Arg Cys Ala Leu Thr Ala Ala His Ser His Leu Phe
385                 390                 395                 400

Gly Gln Leu Lys Glu Phe Glu Lys Lys Pro Glu Gly Ser Ile Pro Glu
                405                 410                 415

Lys Pro Ile Asn Ala Val Lys Asp Arg Val His Gln Ile Glu Glu Val
                420                 425                 430

Leu Ala Lys Pro Val Ile Asp Asp Glu Asp Tyr Lys Lys Leu His Thr
                435                 440                 445

Ala Asn Met Val Arg Lys Cys Ser Lys Ser Lys Gln Ile Leu Ile Ser
450                 455                 460

Arg Pro Pro Leu Leu Ser Ile His Ile Asn Arg Ser Val Phe Asp
465                 470                 475                 480

Pro Arg Thr Tyr Met Ile Arg Lys Asn Asn Ser Lys Val Leu Phe Lys
                485                 490                 495

Ser Arg Leu Asn Leu Ala Pro Trp Cys Cys Asp Ile Asn Glu Ile Asn
                500                 505                 510

Leu Asp Ala Arg Leu Pro Met Ser Lys Lys Glu Lys Ala Ala Gln Gln
                515                 520                 525

Asp Ser Ser Glu Asp Glu Asn Ile Gly Gly Tyr Tyr Thr Lys Leu
530                 535                 540

His Glu Arg Phe Glu Gln Glu Phe Glu Asp Ser Glu Glu Lys Glu
545                 550                 555                 560

Tyr Asp Asp Ala Glu Gly Asn Tyr Ala Ser His Tyr Asn His Thr Lys
                565                 570                 575

Asp Ile Ser Asn Tyr Asp Pro Leu Asn Gly Glu Val Asp Gly Val Thr
                580                 585                 590

Ser Asp Asp Glu Asp Glu Tyr Ile Glu Glu Thr Asp Ala Leu Gly Asn
                595                 600                 605

Thr Ile Lys Lys Arg Ile Ile Glu His Ser Asp Val Glu Asn Glu Asn
                610                 615                 620

Val Lys Asp Asn Glu Glu Leu Gln Glu Ile Asp Asn Val Ser Leu Asp
625                 630                 635                 640

Glu Pro Lys Ile Asn Val Glu Asp Gln Leu Glu Thr Ser Ser Asp Glu
                645                 650                 655

Glu Asp Val Ile Pro Ala Pro Pro Ile Asn Tyr Ala Arg Ser Phe Ser
                660                 665                 670

Thr Val Pro Ala Thr Pro Leu Thr Tyr Ser Leu Arg Ser Val Ile Val
                675                 680                 685

His Tyr Gly Thr His Asn Tyr Gly His Tyr Ile Ala Phe Arg Lys Tyr
                690                 695                 700

Arg Gly Cys Trp Trp Arg Ile Ser Asp Glu Thr Val Tyr Val Val Asp
705                 710                 715                 720
```

```
Glu Ala Glu Val Leu Ser Thr Pro Gly Val Phe Met Leu Phe Tyr Glu
            725                 730                 735

Tyr Asp Phe Asp Glu Glu Thr Gly Lys Met Lys Asp Asp Leu Glu Ala
                740                 745                 750

Ile Gln Ser Asn Asn Glu Glu Asp Asp Glu Lys Glu Gln Glu Gln Lys
            755                 760                 765

Gly Val Gln Glu Pro Lys Glu Ser Gln Glu Gln Gly Glu Gly Glu Glu
            770                 775                 780

Gln Glu Glu Gly Gln Glu Gln Met Lys Phe Glu Arg Thr Glu Asp His
785                 790                 795                 800

Arg Asp Ile Ser Gly Lys Asp Val Asn
            805
```

<210> SEQ ID NO 6  
<211> LENGTH: 2655  
<212> TYPE: DNA  
<213> ORGANISM: artificial sequence  
<220> FEATURE:  
<223> OTHER INFORMATION: UBI+UBP1ABC  
<220> FEATURE:  
<221> NAME/KEY: CDS  
<222> LOCATION: (1)..(2655)  
<223> OTHER INFORMATION: sequence of UBI+UBP1ABC, comprising
      substitutions of: Pro for Leu (415), Phe for Leu (739) and Glu for
      Leu (754)

<400> SEQUENCE: 6

```
atg cag att ttc gtc aaa act ttg acc ggt aaa acc ata aca ttg gaa      48
Met Gln Ile Phe Val Lys Thr Leu Thr Gly Lys Thr Ile Thr Leu Glu
1               5                   10                  15 gtt gaa tct tcc gat acc atc gac aac gtt aag tcg aaa att caa gac      96
Val Glu Ser Ser Asp Thr Ile Asp Asn Val Lys Ser Lys Ile Gln Asp
                20                  25                  30 aag gaa ggt atc cct cca gat caa caa aga ttg atc ttt gcc ggt aag     144
Lys Glu Gly Ile Pro Pro Asp Gln Gln Arg Leu Ile Phe Ala Gly Lys
            35                  40                  45 cag cta gaa gac ggt aga acg ctg tct gat tac aac att cag aag gag     192
Gln Leu Glu Asp Gly Arg Thr Leu Ser Asp Tyr Asn Ile Gln Lys Glu
        50                  55                  60 tcc acc tta cat ctt gtc tta aga ctc cgc ggt ggt gat ttg ttt att     240
Ser Thr Leu His Leu Val Leu Arg Leu Arg Gly Gly Asp Leu Phe Ile
65                  70                  75                  80 gaa agc aag ata aac agt tta tta caa ttt tta ttt ggt tcc cga cag     288
Glu Ser Lys Ile Asn Ser Leu Leu Gln Phe Leu Phe Gly Ser Arg Gln
                85                  90                  95 gat ttt ttg aga aat ttt aaa act tgg agt aac aac aat aac aat cta     336
Asp Phe Leu Arg Asn Phe Lys Thr Trp Ser Asn Asn Asn Asn Asn Leu
            100                 105                 110 tcg att tat tta tta att ttt ggc ata gta gta ttt ttt tat aaa aaa     384
Ser Ile Tyr Leu Leu Ile Phe Gly Ile Val Val Phe Phe Tyr Lys Lys
        115                 120                 125 cca gac cat cta aac tac att gtt gag agc gtt agt gaa atg aca aca     432
Pro Asp His Leu Asn Tyr Ile Val Glu Ser Val Ser Glu Met Thr Thr
    130                 135                 140 aac ttc aga aat aat aat agc ctt agc cgt tgg ttg ccc aga agt aag     480
Asn Phe Arg Asn Asn Asn Ser Leu Ser Arg Trp Leu Pro Arg Ser Lys
145                 150                 155                 160 ttt acc cac tta gac gaa gag atc ttg aaa aga ggt ggt ttc att gct     528
Phe Thr His Leu Asp Glu Glu Ile Leu Lys Arg Gly Gly Phe Ile Ala
                165                 170                 175
```

| | | |
|---|---|---|
| ggt tta gtt aat gat ggt aac act tgt ttt atg aac tct gtt ttg caa<br>Gly Leu Val Asn Asp Gly Asn Thr Cys Phe Met Asn Ser Val Leu Gln<br>180                        185                        190 | 576 |
| tca ttg gca tca tcc aga gaa tta atg gag ttc ttg gac aat aat gtc<br>Ser Leu Ala Ser Ser Arg Glu Leu Met Glu Phe Leu Asp Asn Asn Val<br>195                        200                        205 | 624 |
| ata agg acc tat gag gag ata gaa caa aat gaa cac aat gaa gaa gga<br>Ile Arg Thr Tyr Glu Glu Ile Glu Gln Asn Glu His Asn Glu Glu Gly<br>210                        215                        220 | 672 |
| aac ggg caa gaa tct gct caa gat gaa gcc act cat aag aaa aac act<br>Asn Gly Gln Glu Ser Ala Gln Asp Glu Ala Thr His Lys Lys Asn Thr<br>225                        230                        235                        240 | 720 |
| cgt aag ggt ggc aaa gtt tat ggt aag cat aag aag aaa ttg aat agg<br>Arg Lys Gly Gly Lys Val Tyr Gly Lys His Lys Lys Lys Leu Asn Arg<br>                        245                        250                        255 | 768 |
| aag tca agt tcg aaa gaa gac gaa gaa aag agc cag gag cca gat atc<br>Lys Ser Ser Ser Lys Glu Asp Glu Glu Lys Ser Gln Glu Pro Asp Ile<br>                        260                        265                        270 | 816 |
| act ttc agt gtc gcc tta agg gat cta ctt tct gcc tta aat gcg aag<br>Thr Phe Ser Val Ala Leu Arg Asp Leu Leu Ser Ala Leu Asn Ala Lys<br>          275                        280                        285 | 864 |
| tat tat cgg gat aaa ccc tat ttc aaa acc aat agt tta ttg aaa gca<br>Tyr Tyr Arg Asp Lys Pro Tyr Phe Lys Thr Asn Ser Leu Leu Lys Ala<br>          290                        295                        300 | 912 |
| atg tcc aaa tct cca aga aaa aat att ctt ctt ggc tac gac caa gag<br>Met Ser Lys Ser Pro Arg Lys Asn Ile Leu Leu Gly Tyr Asp Gln Glu<br>305                        310                        315                        320 | 960 |
| gac gcg caa gaa ttc ttc cag aac ata cta gcc gag ttg gaa agt aac<br>Asp Ala Gln Glu Phe Phe Gln Asn Ile Leu Ala Glu Leu Glu Ser Asn<br>                        325                        330                        335 | 1008 |
| gtt aaa tca ttg aat act gaa aaa cta gat acc act cca gtt gcg aaa<br>Val Lys Ser Leu Asn Thr Glu Lys Leu Asp Thr Thr Pro Val Ala Lys<br>                    340                        345                        350 | 1056 |
| tca gaa tta ccc gat gat gct tta gta ggt caa ctt aac ctt ggt gaa<br>Ser Glu Leu Pro Asp Asp Ala Leu Val Gly Gln Leu Asn Leu Gly Glu<br>          355                        360                        365 | 1104 |
| gtt ggc act gtt tac att cca act gaa cag att gat cct aac tct ata<br>Val Gly Thr Val Tyr Ile Pro Thr Glu Gln Ile Asp Pro Asn Ser Ile<br>370                        375                        380 | 1152 |
| cta cat gac aag tcc att caa aat ttc aca cct ttc aaa cta atg act<br>Leu His Asp Lys Ser Ile Gln Asn Phe Thr Pro Phe Lys Leu Met Thr<br>385                        390                        395                        400 | 1200 |
| cct tta gat ggt atc acg gca gaa aga att ggt tgt tta cag tgt ggt<br>Pro Leu Asp Gly Ile Thr Ala Glu Arg Ile Gly Cys Leu Gln Cys Gly<br>                        405                        410                        415 | 1248 |
| gag aac ggt ggc ata aga tat tcc gta ttt tcg gga tta agc tta aat<br>Glu Asn Gly Gly Ile Arg Tyr Ser Val Phe Ser Gly Leu Ser Leu Asn<br>                    420                        425                        430 | 1296 |
| tta ccg aac gag aat att ggt tcc act tta aaa tta tct cag tta tta<br>Leu Pro Asn Glu Asn Ile Gly Ser Thr Leu Lys Leu Ser Gln Leu Leu<br>          435                        440                        445 | 1344 |
| agc gac tgg agt aaa cct gaa atc atc gaa ggc gta gaa tgt aac cgt<br>Ser Asp Trp Ser Lys Pro Glu Ile Ile Glu Gly Val Glu Cys Asn Arg<br>450                        455                        460 | 1392 |
| tgt gcc ctc aca gca gcg cac tct cat tta ttt ggt cag ttg aaa gaa<br>Cys Ala Leu Thr Ala Ala His Ser His Leu Phe Gly Gln Leu Lys Glu<br>465                        470                        475                        480 | 1440 |
| ttt gaa aaa aaa cct gag ggt tcg atc cca gaa aag tta att aac gct<br>Phe Glu Lys Lys Pro Glu Gly Ser Ile Pro Glu Lys Leu Ile Asn Ala<br>                        485                        490                        495 | 1488 |

```
gta aaa gat agg gtc cat caa atc gaa gaa gtt ctt gcc aaa cca gtt       1536
Val Lys Asp Arg Val His Gln Ile Glu Glu Val Leu Ala Lys Pro Val
            500                 505                 510 att gac gat gaa gat tat aag aag ttg cat aca gca aat atg gta cgt       1584
Ile Asp Asp Glu Asp Tyr Lys Lys Leu His Thr Ala Asn Met Val Arg
        515                 520                 525 aaa tgc tct aaa tct aag cag att tta ata tca aga cct cca cca tta       1632
Lys Cys Ser Lys Ser Lys Gln Ile Leu Ile Ser Arg Pro Pro Pro Leu
530                 535                 540 tta tcc att cat atc aac aga tcc gta ttt gat cca aga acg tac atg       1680
Leu Ser Ile His Ile Asn Arg Ser Val Phe Asp Pro Arg Thr Tyr Met
545                 550                 555                 560 att aga aaa aat aac tcg aaa gta ttg ttt aag tca agg ttg aat ctt       1728
Ile Arg Lys Asn Asn Ser Lys Val Leu Phe Lys Ser Arg Leu Asn Leu
                565                 570                 575 gcc cca tgg tgt tgt gat att aat gaa atc aat ttg gat gct cgt ttg       1776
Ala Pro Trp Cys Cys Asp Ile Asn Glu Ile Asn Leu Asp Ala Arg Leu
            580                 585                 590 cca atg tca aaa aag gaa aaa gct gcg caa caa gat tca agt gaa gat       1824
Pro Met Ser Lys Lys Glu Lys Ala Ala Gln Gln Asp Ser Ser Glu Asp
        595                 600                 605 gaa aac att ggc ggt gaa tac tat acg aaa tta cat gaa cgc ttc gag       1872
Glu Asn Ile Gly Gly Glu Tyr Tyr Thr Lys Leu His Glu Arg Phe Glu
610                 615                 620 cag gaa ttt gaa gac agc gag gaa gaa aaa gaa tac gat gac gca gag       1920
Gln Glu Phe Glu Asp Ser Glu Glu Glu Lys Glu Tyr Asp Asp Ala Glu
625                 630                 635                 640 ggg aac tat gcg tct cat tac aat cat acc aag gat atc agt aac tat       1968
Gly Asn Tyr Ala Ser His Tyr Asn His Thr Lys Asp Ile Ser Asn Tyr
                645                 650                 655 gat ccc cta aac ggt gaa gtc gat ggc gtg aca tcc gat gaa gat            2016
Asp Pro Leu Asn Gly Glu Val Asp Gly Val Thr Ser Asp Glu Asp
            660                 665                 670 gag tac att gaa gaa acc gat gct tta ggg aat aca atc aaa aaa agg       2064
Glu Tyr Ile Glu Glu Thr Asp Ala Leu Gly Asn Thr Ile Lys Lys Arg
        675                 680                 685 atc ata gaa cat tct gat gtt gaa aac gag aat gta aaa gat aat gaa       2112
Ile Ile Glu His Ser Asp Val Glu Asn Glu Asn Val Lys Asp Asn Glu
690                 695                 700 gaa ctg caa gaa atc gac aat gtg agc ctt gac gaa cca aag atc aat       2160
Glu Leu Gln Glu Ile Asp Asn Val Ser Leu Asp Glu Pro Lys Ile Asn
705                 710                 715                 720 gtt gaa gat caa cta gaa aca tca tct gat gag gaa gat gtt ata cca       2208
Val Glu Asp Gln Leu Glu Thr Ser Ser Asp Glu Glu Asp Val Ile Pro
                725                 730                 735 gct cca cct atc aat tat gct agg tca ttt tcc aca gtt cca gcc act       2256
Ala Pro Pro Ile Asn Tyr Ala Arg Ser Phe Ser Thr Val Pro Ala Thr
            740                 745                 750 cca ttg aca tat tca ttg cgc tct gtc att gtt cac tac ggt acc cat       2304
Pro Leu Thr Tyr Ser Leu Arg Ser Val Ile Val His Tyr Gly Thr His
        755                 760                 765 aat tat ggt cat tac att gca ttt aga aaa tac agg ggt tgt tgg tgg       2352
Asn Tyr Gly His Tyr Ile Ala Phe Arg Lys Tyr Arg Gly Cys Trp Trp
770                 775                 780 aga ata tct gat gag act gtg tac gtt gtg gac gaa gct gaa gtc ctt       2400
Arg Ile Ser Asp Glu Thr Val Tyr Val Val Asp Glu Ala Glu Val Leu
785                 790                 795                 800 tca aca ccc ggt gta ttt atg tta ttt tac gaa tat gac ctt gat gaa       2448
Ser Thr Pro Gly Val Phe Met Leu Phe Tyr Glu Tyr Asp Leu Asp Glu
```

```
                         805                 810                 815
gaa act ggg aag atg aag gat gat ttg gaa gct att ctg agt aat aat     2496
Glu Thr Gly Lys Met Lys Asp Asp Leu Glu Ala Ile Leu Ser Asn Asn
        820                 825                 830 gaa gaa gat gat gaa aaa gag cag gag caa aaa gga gtc cag gag cca     2544
Glu Glu Asp Asp Glu Lys Glu Gln Glu Gln Lys Gly Val Gln Glu Pro
            835                 840                 845 aag gaa agc caa gag caa gga gaa ggt gaa gag caa gag gaa ggt caa     2592
Lys Glu Ser Gln Glu Gln Gly Glu Gly Glu Glu Gln Glu Glu Gly Gln
        850                 855                 860 gag cag atg aag ttc gag aga aca gaa gac cat aga gat att tct ggt     2640
Glu Gln Met Lys Phe Glu Arg Thr Glu Asp His Arg Asp Ile Ser Gly
865                 870                 875                 880 aaa gat gta aac taa                                                 2655
Lys Asp Val Asn <210> SEQ ID NO 7
<211> LENGTH: 884
<212> TYPE: PRT
<213> ORGANISM: artificial sequence
<220> FEATURE:
<223> OTHER INFORMATION: Synthetic Construct

<400> SEQUENCE: 7

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ser Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Asp Leu Phe Ile
65                  70                  75                  80

Glu Ser Lys Ile Asn Ser Leu Leu Gln Phe Leu Phe Gly Ser Arg Gln
                85                  90                  95

Asp Phe Leu Arg Asn Phe Lys Thr Trp Ser Asn Asn Asn Asn Asn Leu
            100                 105                 110

Ser Ile Tyr Leu Leu Ile Phe Gly Ile Val Val Phe Phe Tyr Lys Lys
        115                 120                 125

Pro Asp His Leu Asn Tyr Ile Val Glu Ser Val Ser Glu Met Thr Thr
    130                 135                 140

Asn Phe Arg Asn Asn Asn Ser Leu Ser Arg Trp Leu Pro Arg Ser Lys
145                 150                 155                 160

Phe Thr His Leu Asp Glu Glu Ile Leu Lys Arg Gly Gly Phe Ile Ala
                165                 170                 175

Gly Leu Val Asn Asp Gly Asn Thr Cys Phe Met Asn Ser Val Leu Gln
            180                 185                 190

Ser Leu Ala Ser Ser Arg Glu Leu Met Glu Phe Leu Asp Asn Asn Val
        195                 200                 205

Ile Arg Thr Tyr Glu Glu Ile Glu Gln Asn Glu His Asn Glu Glu Gly
    210                 215                 220

Asn Gly Gln Glu Ser Ala Gln Asp Glu Ala Thr His Lys Lys Asn Thr
225                 230                 235                 240

Arg Lys Gly Gly Lys Val Tyr Gly Lys His Lys Lys Leu Asn Arg
                245                 250                 255
```

-continued

```
Lys Ser Ser Ser Lys Glu Asp Glu Glu Lys Ser Gln Glu Pro Asp Ile
            260                 265                 270

Thr Phe Ser Val Ala Leu Arg Asp Leu Leu Ser Ala Leu Asn Ala Lys
        275                 280                 285

Tyr Tyr Arg Asp Lys Pro Tyr Phe Lys Thr Asn Ser Leu Leu Lys Ala
    290                 295                 300

Met Ser Lys Ser Pro Arg Lys Asn Ile Leu Leu Gly Tyr Asp Gln Glu
305                 310                 315                 320

Asp Ala Gln Glu Phe Phe Gln Asn Ile Leu Ala Glu Leu Glu Ser Asn
                325                 330                 335

Val Lys Ser Leu Asn Thr Glu Lys Leu Asp Thr Thr Pro Val Ala Lys
            340                 345                 350

Ser Glu Leu Pro Asp Asp Ala Leu Val Gly Gln Leu Asn Leu Gly Glu
        355                 360                 365

Val Gly Thr Val Tyr Ile Pro Thr Glu Gln Ile Asp Pro Asn Ser Ile
    370                 375                 380

Leu His Asp Lys Ser Ile Gln Asn Phe Thr Pro Phe Lys Leu Met Thr
385                 390                 395                 400

Pro Leu Asp Gly Ile Thr Ala Glu Arg Ile Gly Cys Leu Gln Cys Gly
                405                 410                 415

Glu Asn Gly Gly Ile Arg Tyr Ser Val Phe Ser Gly Leu Ser Leu Asn
            420                 425                 430

Leu Pro Asn Glu Asn Ile Gly Ser Thr Leu Lys Leu Ser Gln Leu Leu
        435                 440                 445

Ser Asp Trp Ser Lys Pro Glu Ile Ile Glu Gly Val Glu Cys Asn Arg
    450                 455                 460

Cys Ala Leu Thr Ala Ala His Ser His Leu Phe Gly Gln Leu Lys Glu
465                 470                 475                 480

Phe Glu Lys Lys Pro Glu Gly Ser Ile Pro Glu Lys Leu Ile Asn Ala
                485                 490                 495

Val Lys Asp Arg Val His Gln Ile Glu Glu Val Leu Ala Lys Pro Val
            500                 505                 510

Ile Asp Asp Glu Asp Tyr Lys Lys Leu His Thr Ala Asn Met Val Arg
        515                 520                 525

Lys Cys Ser Lys Ser Lys Gln Ile Leu Ile Ser Arg Pro Pro Leu
    530                 535                 540

Leu Ser Ile His Ile Asn Arg Ser Val Phe Asp Pro Arg Thr Tyr Met
545                 550                 555                 560

Ile Arg Lys Asn Asn Ser Lys Val Leu Phe Lys Ser Arg Leu Asn Leu
                565                 570                 575

Ala Pro Trp Cys Cys Asp Ile Asn Glu Ile Asn Leu Asp Ala Arg Leu
            580                 585                 590

Pro Met Ser Lys Lys Glu Lys Ala Ala Gln Gln Asp Ser Ser Glu Asp
        595                 600                 605

Glu Asn Ile Gly Gly Glu Tyr Tyr Thr Lys Leu His Glu Arg Phe Glu
    610                 615                 620

Gln Glu Phe Glu Asp Ser Glu Glu Lys Glu Tyr Asp Asp Ala Glu
625                 630                 635                 640

Gly Asn Tyr Ala Ser His Tyr Asn His Thr Lys Asp Ile Ser Asn Tyr
                645                 650                 655

Asp Pro Leu Asn Gly Glu Val Asp Gly Val Thr Ser Asp Asp Glu Asp
            660                 665                 670

Glu Tyr Ile Glu Glu Thr Asp Ala Leu Gly Asn Thr Ile Lys Lys Arg
```

```
                675                 680                 685
Ile Ile Glu His Ser Asp Val Glu Asn Glu Asn Val Lys Asp Asn Glu
    690                 695                 700
Glu Leu Gln Glu Ile Asp Asn Val Ser Leu Asp Glu Pro Lys Ile Asn
705                 710                 715                 720
Val Glu Asp Gln Leu Glu Thr Ser Ser Asp Glu Asp Val Ile Pro
                725                 730                 735
Ala Pro Pro Ile Asn Tyr Ala Arg Ser Phe Ser Thr Val Pro Ala Thr
            740                 745                 750
Pro Leu Thr Tyr Ser Leu Arg Ser Val Ile Val His Tyr Gly Thr His
                755                 760                 765
Asn Tyr Gly His Tyr Ile Ala Phe Arg Lys Tyr Arg Gly Cys Trp Trp
            770                 775                 780
Arg Ile Ser Asp Glu Thr Val Tyr Val Val Asp Glu Ala Glu Val Leu
785                 790                 795                 800
Ser Thr Pro Gly Val Phe Met Leu Phe Tyr Glu Tyr Asp Leu Asp Glu
                805                 810                 815
Glu Thr Gly Lys Met Lys Asp Asp Leu Glu Ala Ile Leu Ser Asn Asn
            820                 825                 830
Glu Glu Asp Asp Glu Lys Glu Gln Glu Gln Lys Gly Val Gln Glu Pro
            835                 840                 845
Lys Glu Ser Gln Glu Gln Gly Glu Gly Glu Gln Glu Glu Gly Gln
850                 855                 860
Glu Gln Met Lys Phe Glu Arg Thr Glu Asp His Arg Asp Ile Ser Gly
865                 870                 875                 880
Lys Asp Val Asn
```

```
<210> SEQ ID NO 8
<211> LENGTH: 2655
<212> TYPE: DNA
<213> ORGANISM: artificial sequence
<220> FEATURE:
<223> OTHER INFORMATION: UBI+UBP1BC
<220> FEATURE:
<221> NAME/KEY: CDS
<222> LOCATION: (1)..(2655)
<223> OTHER INFORMATION: sequence of UBI+UBP1BC, comprising
      substitutions of: Phe for Leu (739) and Glu for Leu (754)

<400> SEQUENCE: 8
```

```
atg cag att ttc gtc aaa act ttg acc ggt aaa acc ata aca ttg gaa      48
Met Gln Ile Phe Val Lys Thr Leu Thr Gly Lys Thr Ile Thr Leu Glu
1               5                   10                  15 gtt gaa tct tcc gat acc atc gac aac gtt aag tcg aaa att caa gac      96
Val Glu Ser Ser Asp Thr Ile Asp Asn Val Lys Ser Lys Ile Gln Asp
                20                  25                  30 aag gaa ggt atc cct cca gat caa caa aga ttg atc ttt gcc ggt aag     144
Lys Glu Gly Ile Pro Pro Asp Gln Gln Arg Leu Ile Phe Ala Gly Lys
            35                  40                  45 cag cta gaa gac ggt aga acg ctg tct gat tac aac att cag aag gag     192
Gln Leu Glu Asp Gly Arg Thr Leu Ser Asp Tyr Asn Ile Gln Lys Glu
        50                  55                  60 tcc acc tta cat ctt gtc tta aga ctc cgc ggt ggt gat ttg ttt att     240
Ser Thr Leu His Leu Val Leu Arg Leu Arg Gly Gly Asp Leu Phe Ile
65                  70                  75                  80 gaa agc aag ata aac agt tta tta caa ttt tta ttt ggt tcc cga cag     288
Glu Ser Lys Ile Asn Ser Leu Leu Gln Phe Leu Phe Gly Ser Arg Gln
                85                  90                  95
```

```
gat ttt ttg aga aat ttt aaa act tgg agt aac aac aat aac aat cta      336
Asp Phe Leu Arg Asn Phe Lys Thr Trp Ser Asn Asn Asn Asn Asn Leu
        100                 105                 110 tcg att tat tta tta att ttt ggc ata gta gta ttt ttt tat aaa aaa      384
Ser Ile Tyr Leu Leu Ile Phe Gly Ile Val Val Phe Phe Tyr Lys Lys
        115                 120                 125 cca gac cat cta aac tac att gtt gag agc gtt agt gaa atg aca aca      432
Pro Asp His Leu Asn Tyr Ile Val Glu Ser Val Ser Glu Met Thr Thr
        130                 135                 140 aac ttc aga aat aat aat agc ctt agc cgt tgg ttg ccc aga agt aag      480
Asn Phe Arg Asn Asn Asn Ser Leu Ser Arg Trp Leu Pro Arg Ser Lys
145                 150                 155                 160 ttt acc cac tta gac gaa gag atc ttg aaa aga ggt ggt ttc att gct      528
Phe Thr His Leu Asp Glu Glu Ile Leu Lys Arg Gly Gly Phe Ile Ala
                165                 170                 175 ggt tta gtt aat gat ggt aac act tgt ttt atg aac tct gtt ttg caa      576
Gly Leu Val Asn Asp Gly Asn Thr Cys Phe Met Asn Ser Val Leu Gln
                180                 185                 190 tca ttg gca tca tcc aga gaa tta atg gag ttc ttg gac aat aat gtc      624
Ser Leu Ala Ser Ser Arg Glu Leu Met Glu Phe Leu Asp Asn Asn Val
                195                 200                 205 ata agg acc tat gag gag ata gaa caa aat gaa cac aat gaa gaa gga      672
Ile Arg Thr Tyr Glu Glu Ile Glu Gln Asn Glu His Asn Glu Glu Gly
        210                 215                 220 aac ggg caa gaa tct gct caa gat gaa gcc act cat aag aaa aac act      720
Asn Gly Gln Glu Ser Ala Gln Asp Glu Ala Thr His Lys Lys Asn Thr
225                 230                 235                 240 cgt aag ggt ggc aaa gtt tat ggt aag cat aag aag aaa ttg aat agg      768
Arg Lys Gly Gly Lys Val Tyr Gly Lys His Lys Lys Lys Leu Asn Arg
                245                 250                 255 aag tca agt tcg aaa gaa gac gaa gaa aag agc cag gag cca gat atc      816
Lys Ser Ser Ser Lys Glu Asp Glu Glu Lys Ser Gln Glu Pro Asp Ile
                260                 265                 270 act ttc agt gtc gcc tta agg gat cta ctt tct gcc tta aat gcg aag      864
Thr Phe Ser Val Ala Leu Arg Asp Leu Leu Ser Ala Leu Asn Ala Lys
                275                 280                 285 tat tat cgg gat aaa ccc tat ttc aaa acc aat agt tta ttg aaa gca      912
Tyr Tyr Arg Asp Lys Pro Tyr Phe Lys Thr Asn Ser Leu Leu Lys Ala
        290                 295                 300 atg tcc aaa tct cca aga aaa aat att ctt ctt ggc tac gac caa gag      960
Met Ser Lys Ser Pro Arg Lys Asn Ile Leu Leu Gly Tyr Asp Gln Glu
305                 310                 315                 320 gac gcg caa gaa ttc ttc cag aac ata cta gcc gag ttg gaa agt aac     1008
Asp Ala Gln Glu Phe Phe Gln Asn Ile Leu Ala Glu Leu Glu Ser Asn
                325                 330                 335 gtt aaa tca ttg aat act gaa aaa cta gat acc act cca gtt gcg aaa     1056
Val Lys Ser Leu Asn Thr Glu Lys Leu Asp Thr Thr Pro Val Ala Lys
                340                 345                 350 tca gaa tta ccc gat gat gct tta gta ggt caa ctt aac ctt ggt gaa     1104
Ser Glu Leu Pro Asp Asp Ala Leu Val Gly Gln Leu Asn Leu Gly Glu
                355                 360                 365 gtt ggc act gtt tac att cca act gaa cag att gat cct aac tct ata     1152
Val Gly Thr Val Tyr Ile Pro Thr Glu Gln Ile Asp Pro Asn Ser Ile
        370                 375                 380 cta cat gac aag tcc att caa aat ttc aca cct ttc aaa cta atg act     1200
Leu His Asp Lys Ser Ile Gln Asn Phe Thr Pro Phe Lys Leu Met Thr
385                 390                 395                 400 cct tta gat ggt atc acg gca gaa aga att ggt tgt tta cag tgt ggt     1248
Pro Leu Asp Gly Ile Thr Ala Glu Arg Ile Gly Cys Leu Gln Cys Gly
                405                 410                 415
```

```
gag aac ggt ggc ata aga tat tcc gta ttt tcg gga tta agc tta aat    1296
Glu Asn Gly Gly Ile Arg Tyr Ser Val Phe Ser Gly Leu Ser Leu Asn
            420                 425                 430 tta ccg aac gag aat att ggt tcc act tta aaa tta tct cag tta tta    1344
Leu Pro Asn Glu Asn Ile Gly Ser Thr Leu Lys Leu Ser Gln Leu Leu
        435                 440                 445 agc gac tgg agt aaa cct gaa atc atc gaa ggc gta gaa tgt aac cgt    1392
Ser Asp Trp Ser Lys Pro Glu Ile Ile Glu Gly Val Glu Cys Asn Arg
450                 455                 460 tgt gcc ctc aca gca gcg cac tct cat tta ttt ggt cag ttg aaa gaa    1440
Cys Ala Leu Thr Ala Ala His Ser His Leu Phe Gly Gln Leu Lys Glu
465                 470                 475                 480 ttt gaa aaa aaa cct gag ggt tcg atc cca gaa aag cca att aac gct    1488
Phe Glu Lys Lys Pro Glu Gly Ser Ile Pro Glu Lys Pro Ile Asn Ala
                485                 490                 495 gta aaa gat agg gtc cat caa atc gaa gaa gtt ctt gcc aaa cca gtt    1536
Val Lys Asp Arg Val His Gln Ile Glu Glu Val Leu Ala Lys Pro Val
            500                 505                 510 att gac gat gaa gat tat aag aag ttg cat aca gca aat atg gta cgt    1584
Ile Asp Asp Glu Asp Tyr Lys Lys Leu His Thr Ala Asn Met Val Arg
        515                 520                 525 aaa tgc tct aaa tct aag cag att tta ata tca aga cct cca cca tta    1632
Lys Cys Ser Lys Ser Lys Gln Ile Leu Ile Ser Arg Pro Pro Pro Leu
530                 535                 540 tta tcc att cat atc aac aga tcc gta ttt gat cca aga acg tac atg    1680
Leu Ser Ile His Ile Asn Arg Ser Val Phe Asp Pro Arg Thr Tyr Met
545                 550                 555                 560 att aga aaa aat aac tcg aaa gta ttg ttt aag tca agg ttg aat ctt    1728
Ile Arg Lys Asn Asn Ser Lys Val Leu Phe Lys Ser Arg Leu Asn Leu
                565                 570                 575 gcc cca tgg tgt tgt gat att aat gaa atc aat ttg gat gct cgt ttg    1776
Ala Pro Trp Cys Cys Asp Ile Asn Glu Ile Asn Leu Asp Ala Arg Leu
            580                 585                 590 cca atg tca aaa aag gaa aaa gct gcg caa caa gat tca agt gaa gat    1824
Pro Met Ser Lys Lys Glu Lys Ala Ala Gln Gln Asp Ser Ser Glu Asp
        595                 600                 605 gaa aac att ggc ggt gaa tac tat acg aaa tta cat gaa cgc ttc gag    1872
Glu Asn Ile Gly Gly Glu Tyr Tyr Thr Lys Leu His Glu Arg Phe Glu
610                 615                 620 cag gaa ttt gaa gac agc gag gaa gaa aaa gaa tac gat gac gca gag    1920
Gln Glu Phe Glu Asp Ser Glu Glu Glu Lys Glu Tyr Asp Asp Ala Glu
625                 630                 635                 640 ggg aac tat gcg tct cat tac aat cat acc aag gat atc agt aac tat    1968
Gly Asn Tyr Ala Ser His Tyr Asn His Thr Lys Asp Ile Ser Asn Tyr
                645                 650                 655 gat ccc cta aac ggt gaa gtc gat ggc gtg aca tcc gat gat gaa gat    2016
Asp Pro Leu Asn Gly Glu Val Asp Gly Val Thr Ser Asp Asp Glu Asp
            660                 665                 670 gag tac att gaa gaa acc gat gct tta ggg aat aca atc aaa aaa agg    2064
Glu Tyr Ile Glu Glu Thr Asp Ala Leu Gly Asn Thr Ile Lys Lys Arg
        675                 680                 685 atc ata gaa cat tct gat gtt gaa aac gag aat gta aaa gat aat gaa    2112
Ile Ile Glu His Ser Asp Val Glu Asn Glu Asn Val Lys Asp Asn Glu
690                 695                 700 gaa ctg caa gaa atc gac aat gtg agc ctt gac gaa cca aag atc aat    2160
Glu Leu Gln Glu Ile Asp Asn Val Ser Leu Asp Glu Pro Lys Ile Asn
705                 710                 715                 720 gtt gaa gat caa cta gaa aca tca tct gat gag gaa gat gtt ata cca    2208
Val Glu Asp Gln Leu Glu Thr Ser Ser Asp Glu Glu Asp Val Ile Pro
```

```
                        725                 730                 735
gct cca cct atc aat tat gct agg tca ttt tcc aca gtt cca gcc act       2256
Ala Pro Pro Ile Asn Tyr Ala Arg Ser Phe Ser Thr Val Pro Ala Thr
            740                 745                 750 cca ttg aca tat tca ttg cgc tct gtc att gtt cac tac ggt acc cat       2304
Pro Leu Thr Tyr Ser Leu Arg Ser Val Ile Val His Tyr Gly Thr His
        755                 760                 765 aat tat ggt cat tac att gca ttt aga aaa tac agg ggt tgt tgg tgg       2352
Asn Tyr Gly His Tyr Ile Ala Phe Arg Lys Tyr Arg Gly Cys Trp Trp
    770                 775                 780 aga ata tct gat gag act gtg tac gtt gtg gac gaa gct gaa gtc ctt       2400
Arg Ile Ser Asp Glu Thr Val Tyr Val Val Asp Glu Ala Glu Val Leu
785                 790                 795                 800 tca aca ccc ggt gta ttt atg tta ttt tac gaa tat gac ctt gat gaa       2448
Ser Thr Pro Gly Val Phe Met Leu Phe Tyr Glu Tyr Asp Leu Asp Glu
                805                 810                 815 gaa act ggg aag atg aag gat gat ttg gaa gct att ctg agt aat aat       2496
Glu Thr Gly Lys Met Lys Asp Asp Leu Glu Ala Ile Leu Ser Asn Asn
            820                 825                 830 gaa gaa gat gat gaa aaa gag cag gag caa aaa gga gtc cag gag cca       2544
Glu Glu Asp Asp Glu Lys Glu Gln Glu Gln Lys Gly Val Gln Glu Pro
        835                 840                 845 aag gaa agc caa gag caa gga gaa ggt gaa gag caa gag gaa ggt caa       2592
Lys Glu Ser Gln Glu Gln Gly Glu Gly Glu Glu Gln Glu Glu Gly Gln
    850                 855                 860 gag cag atg aag ttc gag aga aca gaa gac cat aga gat att tct ggt       2640
Glu Gln Met Lys Phe Glu Arg Thr Glu Asp His Arg Asp Ile Ser Gly
865                 870                 875                 880 aaa gat gta aac taa                                                   2655
Lys Asp Val Asn <210> SEQ ID NO 9
<211> LENGTH: 884
<212> TYPE: PRT
<213> ORGANISM: artificial sequence
<220> FEATURE:
<223> OTHER INFORMATION: Synthetic Construct

<400> SEQUENCE: 9

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ser Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Asp Leu Phe Ile
65                  70                  75                  80

Glu Ser Lys Ile Asn Ser Leu Leu Gln Phe Leu Phe Gly Ser Arg Gln
                85                  90                  95

Asp Phe Leu Arg Asn Phe Lys Thr Trp Ser Asn Asn Asn Asn Asn Leu
            100                 105                 110

Ser Ile Tyr Leu Leu Ile Phe Gly Ile Val Val Phe Tyr Lys Lys
        115                 120                 125

Pro Asp His Leu Asn Tyr Ile Val Glu Ser Val Ser Glu Met Thr Thr
    130                 135                 140

Asn Phe Arg Asn Asn Asn Ser Leu Ser Arg Trp Leu Pro Arg Ser Lys
```

-continued

```
            145                 150                 155                 160
        Phe Thr His Leu Asp Glu Glu Ile Leu Lys Arg Gly Gly Phe Ile Ala
                        165                 170                 175
        Gly Leu Val Asn Asp Gly Asn Thr Cys Phe Met Asn Ser Val Leu Gln
                        180                 185                 190
        Ser Leu Ala Ser Ser Arg Glu Leu Met Glu Phe Leu Asp Asn Asn Val
                        195                 200                 205
        Ile Arg Thr Tyr Glu Glu Ile Glu Gln Asn Glu His Asn Glu Glu Gly
            210                 215                 220
        Asn Gly Gln Glu Ser Ala Gln Asp Glu Ala Thr His Lys Lys Asn Thr
        225                 230                 235                 240
        Arg Lys Gly Gly Lys Val Tyr Gly Lys His Lys Lys Leu Asn Arg
                        245                 250                 255
        Lys Ser Ser Lys Glu Asp Glu Glu Lys Ser Gln Glu Pro Asp Ile
                        260                 265                 270
        Thr Phe Ser Val Ala Leu Arg Asp Leu Leu Ser Ala Leu Asn Ala Lys
                        275                 280                 285
        Tyr Tyr Arg Asp Lys Pro Tyr Phe Lys Thr Asn Ser Leu Leu Lys Ala
                        290                 295                 300
        Met Ser Lys Ser Pro Arg Lys Asn Ile Leu Leu Gly Tyr Asp Gln Glu
        305                 310                 315                 320
        Asp Ala Gln Glu Phe Phe Gln Asn Ile Leu Ala Glu Leu Glu Ser Asn
                        325                 330                 335
        Val Lys Ser Leu Asn Thr Glu Lys Leu Asp Thr Thr Pro Val Ala Lys
                        340                 345                 350
        Ser Glu Leu Pro Asp Asp Ala Leu Val Gly Gln Leu Asn Leu Gly Glu
                        355                 360                 365
        Val Gly Thr Val Tyr Ile Pro Thr Glu Gln Ile Asp Pro Asn Ser Ile
                        370                 375                 380
        Leu His Asp Lys Ser Ile Gln Asn Phe Thr Pro Phe Lys Leu Met Thr
        385                 390                 395                 400
        Pro Leu Asp Gly Ile Thr Ala Glu Arg Ile Gly Cys Leu Gln Cys Gly
                        405                 410                 415
        Glu Asn Gly Gly Ile Arg Tyr Ser Val Phe Ser Gly Leu Ser Leu Asn
                        420                 425                 430
        Leu Pro Asn Glu Asn Ile Gly Ser Thr Leu Lys Leu Ser Gln Leu Leu
                        435                 440                 445
        Ser Asp Trp Ser Lys Pro Glu Ile Ile Glu Gly Val Glu Cys Asn Arg
        450                 455                 460
        Cys Ala Leu Thr Ala Ala His Ser His Leu Phe Gly Gln Leu Lys Glu
        465                 470                 475                 480
        Phe Glu Lys Lys Pro Glu Gly Ser Ile Pro Lys Pro Ile Asn Ala
                        485                 490                 495
        Val Lys Asp Arg Val His Gln Ile Glu Glu Val Leu Ala Lys Pro Val
                        500                 505                 510
        Ile Asp Asp Glu Asp Tyr Lys Lys Leu His Thr Ala Asn Met Val Arg
                        515                 520                 525
        Lys Cys Ser Lys Ser Lys Gln Ile Leu Ile Ser Arg Pro Pro Leu
                        530                 535                 540
        Leu Ser Ile His Ile Asn Arg Ser Val Phe Asp Pro Arg Thr Tyr Met
        545                 550                 555                 560
        Ile Arg Lys Asn Asn Ser Lys Val Leu Phe Lys Ser Arg Leu Asn Leu
                        565                 570                 575
```

-continued

```
Ala Pro Trp Cys Cys Asp Ile Asn Glu Ile Asn Leu Asp Ala Arg Leu
            580                 585                 590

Pro Met Ser Lys Lys Glu Lys Ala Ala Gln Gln Asp Ser Ser Glu Asp
595                 600                 605

Glu Asn Ile Gly Gly Tyr Tyr Thr Lys Leu His Glu Arg Phe Glu
    610                 615                 620

Gln Glu Phe Glu Asp Ser Glu Glu Lys Glu Tyr Asp Asp Ala Glu
625                 630                 635                 640

Gly Asn Tyr Ala Ser His Tyr Asn His Thr Lys Asp Ile Ser Asn Tyr
            645                 650                 655

Asp Pro Leu Asn Gly Glu Val Asp Gly Val Thr Ser Asp Glu Asp
            660                 665                 670

Glu Tyr Ile Glu Glu Thr Asp Ala Leu Gly Asn Thr Ile Lys Lys Arg
            675                 680                 685

Ile Ile Glu His Ser Asp Val Glu Asn Glu Asn Val Lys Asp Asn Glu
    690                 695                 700

Glu Leu Gln Glu Ile Asp Asn Val Ser Leu Asp Glu Pro Lys Ile Asn
705                 710                 715                 720

Val Glu Asp Gln Leu Glu Thr Ser Ser Asp Glu Glu Asp Val Ile Pro
            725                 730                 735

Ala Pro Pro Ile Asn Tyr Ala Arg Ser Phe Ser Thr Val Pro Ala Thr
            740                 745                 750

Pro Leu Thr Tyr Ser Leu Arg Ser Val Ile Val His Tyr Gly Thr His
            755                 760                 765

Asn Tyr Gly His Tyr Ile Ala Phe Arg Lys Tyr Arg Gly Cys Trp Trp
770                 775                 780

Arg Ile Ser Asp Glu Thr Val Tyr Val Asp Glu Ala Glu Val Leu
785                 790                 795                 800

Ser Thr Pro Gly Val Phe Met Leu Phe Tyr Glu Tyr Asp Leu Asp Glu
            805                 810                 815

Glu Thr Gly Lys Met Lys Asp Asp Leu Glu Ala Ile Leu Ser Asn Asn
            820                 825                 830

Glu Glu Asp Asp Glu Lys Glu Gln Glu Gln Lys Gly Val Gln Glu Pro
            835                 840                 845

Lys Glu Ser Gln Glu Gln Gly Glu Gly Glu Gln Glu Gly Gln
850                 855                 860

Glu Gln Met Lys Phe Glu Arg Thr Gly Asp His Arg Asp Ile Ser Gly
865                 870                 875                 880

Lys Asp Val Asn
```

<210> SEQ ID NO 10
<211> LENGTH: 2655
<212> TYPE: DNA
<213> ORGANISM: artificial sequence
<220> FEATURE:
<223> OTHER INFORMATION: UBI+UBP1C
<220> FEATURE:
<221> NAME/KEY: CDS
<222> LOCATION: (1)..(2655)
<223> OTHER INFORMATION: UBI+UBP1C, the mutation is a substitution of
glutamine for leucine (position 754) sequence of UBI+UBP1C,
comprising substitution of Glu for Leu (75 4)

<400> SEQUENCE: 10

```
atg cag att ttc gtc aaa act ttg acc ggt aaa acc ata aca ttg gaa      48
Met Gln Ile Phe Val Lys Thr Leu Thr Gly Lys Thr Ile Thr Leu Glu
1               5                   10                  15
```

| | | | | | | | | | | | | | | | | |
|---|---|---|---|---|---|---|---|---|---|---|---|---|---|---|---|---|
| gtt | gaa | tct | tcc | gat | acc | atc | gac | aac | gtt | aag | tcg | aaa | att | caa | gac | 96 |
| Val | Glu | Ser | Ser | Asp | Thr | Ile | Asp | Asn | Val | Lys | Ser | Lys | Ile | Gln | Asp | |
| | | | 20 | | | | | 25 | | | | | 30 | | | |
| aag | gaa | ggt | atc | cct | cca | gat | caa | caa | aga | ttg | atc | ttt | gcc | ggt | aag | 144 |
| Lys | Glu | Gly | Ile | Pro | Pro | Asp | Gln | Gln | Arg | Leu | Ile | Phe | Ala | Gly | Lys | |
| | | 35 | | | | | 40 | | | | | 45 | | | | |
| cag | cta | gaa | gac | ggt | aga | acg | ctg | tct | gat | tac | aac | att | cag | aag | gag | 192 |
| Gln | Leu | Glu | Asp | Gly | Arg | Thr | Leu | Ser | Asp | Tyr | Asn | Ile | Gln | Lys | Glu | |
| | 50 | | | | | 55 | | | | | 60 | | | | | |
| tcc | acc | tta | cat | ctt | gtc | tta | aga | ctc | cgc | ggt | ggt | gat | ttg | ttt | att | 240 |
| Ser | Thr | Leu | His | Leu | Val | Leu | Arg | Leu | Arg | Gly | Gly | Asp | Leu | Phe | Ile | |
| 65 | | | | 70 | | | | | 75 | | | | | 80 | | |
| gaa | agc | aag | ata | aac | agt | tta | tta | caa | ttt | tta | ttt | ggt | tcc | cga | cag | 288 |
| Glu | Ser | Lys | Ile | Asn | Ser | Leu | Leu | Gln | Phe | Leu | Phe | Gly | Ser | Arg | Gln | |
| | | | | 85 | | | | | 90 | | | | | 95 | | |
| gat | ttt | ttg | aga | aat | ttt | aaa | act | tgg | agt | aac | aac | aat | aac | aat | cta | 336 |
| Asp | Phe | Leu | Arg | Asn | Phe | Lys | Thr | Trp | Ser | Asn | Asn | Asn | Asn | Asn | Leu | |
| | | | 100 | | | | | 105 | | | | | 110 | | | |
| tcg | att | tat | tta | tta | att | ttt | ggc | ata | gta | gta | ttt | ttt | tat | aaa | aaa | 384 |
| Ser | Ile | Tyr | Leu | Leu | Ile | Phe | Gly | Ile | Val | Val | Phe | Phe | Tyr | Lys | Lys | |
| | | 115 | | | | | 120 | | | | | 125 | | | | |
| cca | gac | cat | cta | aac | tac | att | gtt | gag | agc | gtt | agt | gaa | atg | aca | aca | 432 |
| Pro | Asp | His | Leu | Asn | Tyr | Ile | Val | Glu | Ser | Val | Ser | Glu | Met | Thr | Thr | |
| | 130 | | | | | 135 | | | | | 140 | | | | | |
| aac | ttc | aga | aat | aat | aat | agc | ctt | agc | cgt | tgg | ttg | ccc | aga | agt | aag | 480 |
| Asn | Phe | Arg | Asn | Asn | Asn | Ser | Leu | Ser | Arg | Trp | Leu | Pro | Arg | Ser | Lys | |
| 145 | | | | | 150 | | | | | 155 | | | | | 160 | |
| ttt | acc | cac | tta | gac | gaa | gag | atc | ttg | aaa | aga | ggt | ggt | ttc | att | gct | 528 |
| Phe | Thr | His | Leu | Asp | Glu | Glu | Ile | Leu | Lys | Arg | Gly | Gly | Phe | Ile | Ala | |
| | | | | 165 | | | | | 170 | | | | | 175 | | |
| ggt | tta | gtt | aat | gat | ggt | aac | act | tgt | ttt | atg | aac | tct | gtt | ttg | caa | 576 |
| Gly | Leu | Val | Asn | Asp | Gly | Asn | Thr | Cys | Phe | Met | Asn | Ser | Val | Leu | Gln | |
| | | | 180 | | | | | 185 | | | | | 190 | | | |
| tca | ttg | gca | tca | tcc | aga | gaa | tta | atg | gag | ttc | ttg | gac | aat | aat | gtc | 624 |
| Ser | Leu | Ala | Ser | Ser | Arg | Glu | Leu | Met | Glu | Phe | Leu | Asp | Asn | Asn | Val | |
| | | 195 | | | | | 200 | | | | | 205 | | | | |
| ata | agg | acc | tat | gag | gag | ata | gaa | caa | aat | gaa | cac | aat | gaa | gaa | gga | 672 |
| Ile | Arg | Thr | Tyr | Glu | Glu | Ile | Glu | Gln | Asn | Glu | His | Asn | Glu | Glu | Gly | |
| 210 | | | | | 215 | | | | | 220 | | | | | | |
| aac | ggg | caa | gaa | tct | gct | caa | gat | gaa | gcc | act | cat | aag | aaa | aac | act | 720 |
| Asn | Gly | Gln | Glu | Ser | Ala | Gln | Asp | Glu | Ala | Thr | His | Lys | Lys | Asn | Thr | |
| 225 | | | | | 230 | | | | | 235 | | | | | 240 | |
| cgt | aag | ggt | ggc | aaa | gtt | tat | ggt | aag | cat | aag | aag | aaa | ttg | aat | agg | 768 |
| Arg | Lys | Gly | Gly | Lys | Val | Tyr | Gly | Lys | His | Lys | Lys | Lys | Leu | Asn | Arg | |
| | | | | 245 | | | | | 250 | | | | | 255 | | |
| aag | tca | agt | tcg | aaa | gaa | gac | gaa | gaa | aag | agc | cag | gag | cca | gat | atc | 816 |
| Lys | Ser | Ser | Ser | Lys | Glu | Asp | Glu | Glu | Lys | Ser | Gln | Glu | Pro | Asp | Ile | |
| | | | 260 | | | | | 265 | | | | | 270 | | | |
| act | ttc | agt | gtc | gcc | tta | agg | gat | cta | ctt | tct | gcc | tta | aat | gcg | aag | 864 |
| Thr | Phe | Ser | Val | Ala | Leu | Arg | Asp | Leu | Leu | Ser | Ala | Leu | Asn | Ala | Lys | |
| | | 275 | | | | | 280 | | | | | 285 | | | | |
| tat | tat | cgg | gat | aaa | ccc | tat | ttc | aaa | acc | aat | agt | tta | ttg | aaa | gca | 912 |
| Tyr | Tyr | Arg | Asp | Lys | Pro | Tyr | Phe | Lys | Thr | Asn | Ser | Leu | Leu | Lys | Ala | |
| | 290 | | | | | 295 | | | | | 300 | | | | | |
| atg | tcc | aaa | tct | cca | aga | aaa | aat | att | ctt | ctt | ggc | tac | gac | caa | gag | 960 |
| Met | Ser | Lys | Ser | Pro | Arg | Lys | Asn | Ile | Leu | Leu | Gly | Tyr | Asp | Gln | Glu | |
| 305 | | | | 310 | | | | | 315 | | | | | 320 | | |
| gac | gcg | caa | gaa | ttc | ttc | cag | aac | ata | cta | gcc | gag | ttg | gaa | agt | aac | 1008 |
| Asp | Ala | Gln | Glu | Phe | Phe | Gln | Asn | Ile | Leu | Ala | Glu | Leu | Glu | Ser | Asn | |

-continued

```
                    325                 330                 335
gtt aaa tca ttg aat act gaa aaa cta gat acc act cca gtt gcg aaa    1056
Val Lys Ser Leu Asn Thr Glu Lys Leu Asp Thr Thr Pro Val Ala Lys
        340                 345                 350 tca gaa tta ccc gat gat gct tta gta ggt caa ctt aac ctt ggt gaa    1104
Ser Glu Leu Pro Asp Asp Ala Leu Val Gly Gln Leu Asn Leu Gly Glu
            355                 360                 365 gtt ggc act gtt tac att cca act gaa cag att gat cct aac tct ata    1152
Val Gly Thr Val Tyr Ile Pro Thr Glu Gln Ile Asp Pro Asn Ser Ile
370                 375                 380 cta cat gac aag tcc att caa aat ttc aca cct ttc aaa cta atg act    1200
Leu His Asp Lys Ser Ile Gln Asn Phe Thr Pro Phe Lys Leu Met Thr
385                 390                 395                 400 cct tta gat ggt atc acg gca gaa aga att ggt tgt tta cag tgt ggt    1248
Pro Leu Asp Gly Ile Thr Ala Glu Arg Ile Gly Cys Leu Gln Cys Gly
                405                 410                 415 gag aac ggt ggc ata aga tat tcc gta ttt tcg gga tta agc tta aat    1296
Glu Asn Gly Gly Ile Arg Tyr Ser Val Phe Ser Gly Leu Ser Leu Asn
                420                 425                 430 tta ccg aac gag aat att ggt tcc act tta aaa tta tct cag tta tta    1344
Leu Pro Asn Glu Asn Ile Gly Ser Thr Leu Lys Leu Ser Gln Leu Leu
            435                 440                 445 agc gac tgg agt aaa cct gaa atc atc gaa ggc gta gaa tgt aac cgt    1392
Ser Asp Trp Ser Lys Pro Glu Ile Ile Glu Gly Val Glu Cys Asn Arg
450                 455                 460 tgt gcc ctc aca gca gcg cac tct cat tta ttt ggt cag ttg aaa gaa    1440
Cys Ala Leu Thr Ala Ala His Ser His Leu Phe Gly Gln Leu Lys Glu
465                 470                 475                 480 ttt gaa aaa aaa cct gag ggt tcg atc cca gaa aag cca att aac gct    1488
Phe Glu Lys Lys Pro Glu Gly Ser Ile Pro Glu Lys Pro Ile Asn Ala
                485                 490                 495 gta aaa gat agg gtc cat caa atc gaa gaa gtt ctt gcc aaa cca gtt    1536
Val Lys Asp Arg Val His Gln Ile Glu Glu Val Leu Ala Lys Pro Val
            500                 505                 510 att gac gat gaa gat tat aag aag ttg cat aca gca aat atg gta cgt    1584
Ile Asp Asp Glu Asp Tyr Lys Lys Leu His Thr Ala Asn Met Val Arg
        515                 520                 525 aaa tgc tct aaa tct aag cag att tta ata tca aga cct cca cca tta    1632
Lys Cys Ser Lys Ser Lys Gln Ile Leu Ile Ser Arg Pro Pro Pro Leu
530                 535                 540 tta tcc att cat atc aac aga tcc gta ttt gat cca aga acg tac atg    1680
Leu Ser Ile His Ile Asn Arg Ser Val Phe Asp Pro Arg Thr Tyr Met
545                 550                 555                 560 att aga aaa aat aac tcg aaa gta ttg ttt aag tca agg ttg aat ctt    1728
Ile Arg Lys Asn Asn Ser Lys Val Leu Phe Lys Ser Arg Leu Asn Leu
                565                 570                 575 gcc cca tgg tgt tgt gat att aat gaa atc aat ttg gat gct cgt ttg    1776
Ala Pro Trp Cys Cys Asp Ile Asn Glu Ile Asn Leu Asp Ala Arg Leu
            580                 585                 590 cca atg tca aaa aag gaa aaa gct gcg caa caa gat tca agt gaa gat    1824
Pro Met Ser Lys Lys Glu Lys Ala Ala Gln Gln Asp Ser Ser Glu Asp
        595                 600                 605 gaa aac att ggc ggt gaa tac tat acg aaa tta cat gaa cgc ttc gag    1872
Glu Asn Ile Gly Gly Glu Tyr Tyr Thr Lys Leu His Glu Arg Phe Glu
610                 615                 620 cag gaa ttt gaa gac agc gag gaa gaa aaa gaa tac gat gac gca gag    1920
Gln Glu Phe Glu Asp Ser Glu Glu Glu Lys Glu Tyr Asp Asp Ala Glu
625                 630                 635                 640 ggg aac tat gcg tct cat tac aat cat acc aag gat atc agt aac tat    1968
```

```
                Gly Asn Tyr Ala Ser His Tyr Asn His Thr Lys Asp Ile Ser Asn Tyr
                                645                 650                 655 gat ccc cta aac ggt gaa gtc gat ggc gtg aca tcc gat gat gaa gat          2016
Asp Pro Leu Asn Gly Glu Val Asp Gly Val Thr Ser Asp Asp Glu Asp
            660                 665                 670 gag tac att gaa gaa acc gat gct tta ggg aat aca atc aaa aaa agg          2064
Glu Tyr Ile Glu Glu Thr Asp Ala Leu Gly Asn Thr Ile Lys Lys Arg
        675                 680                 685 atc ata gaa cat tct gat gtt gaa aac gag aat gta aaa gat aat gaa          2112
Ile Ile Glu His Ser Asp Val Glu Asn Glu Asn Val Lys Asp Asn Glu
    690                 695                 700 gaa ctg caa gaa atc gac aat gtg agc ctt gac gaa cca aag atc aat          2160
Glu Leu Gln Glu Ile Asp Asn Val Ser Leu Asp Glu Pro Lys Ile Asn
705                 710                 715                 720 gtt gaa gat caa cta gaa aca tca tct gat gag gaa gat gtt ata cca          2208
Val Glu Asp Gln Leu Glu Thr Ser Ser Asp Glu Glu Asp Val Ile Pro
                725                 730                 735 gct cca cct atc aat tat gct agg tca ttt tcc aca gtt cca gcc act          2256
Ala Pro Pro Ile Asn Tyr Ala Arg Ser Phe Ser Thr Val Pro Ala Thr
            740                 745                 750 cca ttg aca tat tca ttg cgc tct gtc att gtt cac tac ggt acc cat          2304
Pro Leu Thr Tyr Ser Leu Arg Ser Val Ile Val His Tyr Gly Thr His
        755                 760                 765 aat tat ggt cat tac att gca ttt aga aaa tac agg ggt tgt tgg tgg          2352
Asn Tyr Gly His Tyr Ile Ala Phe Arg Lys Tyr Arg Gly Cys Trp Trp
    770                 775                 780 aga ata tct gat gag act gtg tac gtt gtg gac gaa gct gaa gtc ctt          2400
Arg Ile Ser Asp Glu Thr Val Tyr Val Val Asp Glu Ala Glu Val Leu
785                 790                 795                 800 tca aca ccc ggt gta ttt atg tta ttt tac gaa tat gac ttt gat gaa          2448
Ser Thr Pro Gly Val Phe Met Leu Phe Tyr Glu Tyr Asp Phe Asp Glu
                805                 810                 815 gaa act ggg aag atg aag gat gat ttg gaa gct att ctg agt aat aat          2496
Glu Thr Gly Lys Met Lys Asp Asp Leu Glu Ala Ile Leu Ser Asn Asn
            820                 825                 830 gaa gaa gat gat gaa aaa gag cag gag caa aaa gga gtc cag gag cca          2544
Glu Glu Asp Asp Glu Lys Glu Gln Glu Gln Lys Gly Val Gln Glu Pro
        835                 840                 845 aag gaa agc caa gag caa gga gaa ggt gaa gag caa gag gaa ggt caa          2592
Lys Glu Ser Gln Glu Gln Gly Glu Gly Glu Gln Glu Glu Gly Gln
    850                 855                 860 gag cag atg aag ttc gag aga aca gaa gac cat aga gat att tct ggt          2640
Glu Gln Met Lys Phe Glu Arg Thr Glu Asp His Arg Asp Ile Ser Gly
865                 870                 875                 880 aaa gat gta aac taa                                                      2655
Lys Asp Val Asn <210> SEQ ID NO 11
<211> LENGTH: 884
<212> TYPE: PRT
<213> ORGANISM: artificial sequence
<220> FEATURE:
<223> OTHER INFORMATION: Synthetic Construct

<400> SEQUENCE: 11

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ser Lys Ile Gln Asp
            20                  25                  30

Lys Glu Gly Ile Pro Pro Asp Gln Gln Arg Leu Ile Phe Ala Gly Lys
```

```
                35                  40                  45
Gln Leu Glu Asp Gly Arg Thr Leu Ser Asp Tyr Asn Ile Gln Lys Glu
 50                  55                  60

Ser Thr Leu His Leu Val Leu Arg Leu Arg Gly Gly Asp Leu Phe Ile
 65                  70                  75                  80

Glu Ser Lys Ile Asn Ser Leu Leu Gln Phe Leu Phe Gly Ser Arg Gln
                 85                  90                  95

Asp Phe Leu Arg Asn Phe Lys Thr Trp Ser Asn Asn Asn Asn Asn Leu
            100                 105                 110

Ser Ile Tyr Leu Leu Ile Phe Gly Ile Val Val Phe Phe Tyr Lys Lys
        115                 120                 125

Pro Asp His Leu Asn Tyr Ile Val Glu Ser Val Ser Glu Met Thr Thr
    130                 135                 140

Asn Phe Arg Asn Asn Ser Leu Ser Arg Trp Leu Pro Arg Ser Lys
145                 150                 155                 160

Phe Thr His Leu Asp Glu Glu Ile Leu Lys Arg Gly Gly Phe Ile Ala
                165                 170                 175

Gly Leu Val Asn Asp Gly Asn Thr Cys Phe Met Asn Ser Val Leu Gln
            180                 185                 190

Ser Leu Ala Ser Ser Arg Glu Leu Met Glu Phe Leu Asp Asn Asn Val
        195                 200                 205

Ile Arg Thr Tyr Glu Glu Ile Glu Gln Asn Glu His Asn Glu Glu Gly
    210                 215                 220

Asn Gly Gln Glu Ser Ala Gln Asp Glu Ala Thr His Lys Lys Asn Thr
225                 230                 235                 240

Arg Lys Gly Gly Lys Val Tyr Gly Lys His Lys Lys Leu Asn Arg
                245                 250                 255

Lys Ser Ser Ser Lys Glu Asp Glu Glu Lys Ser Gln Glu Pro Asp Ile
            260                 265                 270

Thr Phe Ser Val Ala Leu Arg Asp Leu Leu Ser Ala Leu Asn Ala Lys
        275                 280                 285

Tyr Tyr Arg Asp Lys Pro Tyr Phe Lys Thr Asn Ser Leu Leu Lys Ala
    290                 295                 300

Met Ser Lys Ser Pro Arg Lys Asn Ile Leu Leu Gly Tyr Asp Gln Glu
305                 310                 315                 320

Asp Ala Gln Glu Phe Phe Gln Asn Ile Leu Ala Glu Leu Glu Ser Asn
                325                 330                 335

Val Lys Ser Leu Asn Thr Glu Lys Leu Asp Thr Thr Pro Val Ala Lys
            340                 345                 350

Ser Glu Leu Pro Asp Asp Ala Leu Val Gly Gln Leu Asn Leu Gly Glu
        355                 360                 365

Val Gly Thr Val Tyr Ile Pro Thr Glu Gln Ile Asp Pro Asn Ser Ile
    370                 375                 380

Leu His Asp Lys Ser Ile Gln Asn Phe Thr Pro Phe Lys Leu Met Thr
385                 390                 395                 400

Pro Leu Asp Gly Ile Thr Ala Glu Arg Ile Gly Cys Leu Gln Cys Gly
                405                 410                 415

Glu Asn Gly Gly Ile Arg Tyr Ser Val Phe Ser Gly Leu Ser Leu Asn
            420                 425                 430

Leu Pro Asn Glu Asn Ile Gly Ser Thr Leu Lys Leu Ser Gln Leu Leu
        435                 440                 445

Ser Asp Trp Ser Lys Pro Glu Ile Ile Glu Gly Val Glu Cys Asn Arg
    450                 455                 460
```

-continued

Cys Ala Leu Thr Ala Ala His Ser His Leu Phe Gly Gln Leu Lys Glu
465                 470                 475                 480

Phe Glu Lys Lys Pro Glu Gly Ser Ile Pro Glu Lys Pro Ile Asn Ala
            485                 490                 495

Val Lys Asp Arg Val His Gln Ile Glu Glu Val Leu Ala Lys Pro Val
        500                 505                 510

Ile Asp Asp Glu Asp Tyr Lys Lys Leu His Thr Ala Asn Met Val Arg
    515                 520                 525

Lys Cys Ser Lys Ser Lys Gln Ile Leu Ile Ser Arg Pro Pro Leu
530                 535                 540

Leu Ser Ile His Ile Asn Arg Ser Val Phe Asp Pro Arg Thr Tyr Met
545                 550                 555                 560

Ile Arg Lys Asn Asn Ser Lys Val Leu Phe Lys Ser Arg Leu Asn Leu
                565                 570                 575

Ala Pro Trp Cys Cys Asp Ile Asn Glu Ile Asn Leu Asp Ala Arg Leu
                580                 585                 590

Pro Met Ser Lys Lys Glu Lys Ala Ala Gln Gln Asp Ser Ser Glu Asp
            595                 600                 605

Glu Asn Ile Gly Gly Glu Tyr Tyr Thr Lys Leu His Glu Arg Phe Glu
610                 615                 620

Gln Glu Phe Glu Asp Ser Glu Glu Lys Glu Tyr Asp Asp Ala Glu
625                 630                 635                 640

Gly Asn Tyr Ala Ser His Tyr Asn His Thr Lys Asp Ile Ser Asn Tyr
                645                 650                 655

Asp Pro Leu Asn Gly Glu Val Asp Gly Val Thr Ser Asp Glu Asp
            660                 665                 670

Glu Tyr Ile Glu Glu Thr Asp Ala Leu Gly Asn Thr Ile Lys Lys Arg
            675                 680                 685

Ile Ile Glu His Ser Asp Val Glu Asn Glu Asn Val Lys Asp Asn Glu
            690                 695                 700

Glu Leu Gln Glu Ile Asp Asn Val Ser Leu Asp Glu Pro Lys Ile Asn
705                 710                 715                 720

Val Glu Asp Gln Leu Glu Thr Ser Ser Asp Glu Glu Asp Val Ile Pro
                725                 730                 735

Ala Pro Pro Ile Asn Tyr Ala Arg Ser Phe Ser Thr Val Pro Ala Thr
            740                 745                 750

Pro Leu Thr Tyr Ser Leu Arg Ser Val Ile Val His Tyr Gly Thr His
            755                 760                 765

Asn Tyr Gly His Tyr Ile Ala Phe Arg Lys Tyr Arg Gly Cys Trp Trp
            770                 775                 780

Arg Ile Ser Asp Glu Thr Val Tyr Val Asp Glu Ala Glu Val Leu
785                 790                 795                 800

Ser Thr Pro Gly Val Phe Met Leu Phe Tyr Glu Tyr Asp Phe Asp Glu
                805                 810                 815

Glu Thr Gly Lys Met Lys Asp Asp Leu Glu Ala Ile Leu Ser Asn Asn
            820                 825                 830

Glu Glu Asp Asp Glu Lys Glu Gln Glu Gln Lys Gly Val Gln Glu Pro
            835                 840                 845

Lys Glu Ser Gln Glu Gln Gly Glu Gly Glu Glu Gln Glu Glu Gly Gln
            850                 855                 860

Glu Gln Met Lys Phe Glu Arg Thr Glu Asp His Arg Asp Ile Ser Gly
865                 870                 875                 880

Lys Asp Val Asn

<210> SEQ ID NO 12
<211> LENGTH: 39
<212> TYPE: DNA
<213> ORGANISM: Artificial Sequence
<220> FEATURE:
<223> OTHER INFORMATION: primer

<400> SEQUENCE: 12
agactccgcg gtggtgattt gtttattgaa agcaagata          39

<210> SEQ ID NO 13
<211> LENGTH: 33
<212> TYPE: DNA
<213> ORGANISM: Artificial Sequence
<220> FEATURE:
<223> OTHER INFORMATION: primer

<400> SEQUENCE: 13
ggggatcctt agtttacatc tttaccagaa ata               33

<210> SEQ ID NO 14
<211> LENGTH: 50
<212> TYPE: DNA
<213> ORGANISM: Artificial Sequence
<220> FEATURE:
<223> OTHER INFORMATION: primer

<400> SEQUENCE: 14
ggcatagtag tatttttta ccgcggtggt gaccatctaa actacattgt    50

<210> SEQ ID NO 15
<211> LENGTH: 50
<212> TYPE: DNA
<213> ORGANISM: Artificial Sequence
<220> FEATURE:
<223> OTHER INFORMATION: primer

<400> SEQUENCE: 15
acaatgtagt ttagatggtc accaccgcgg taaaaaaata ctactatgcc    50

UBP1 PROTEASE MUTANT, AND ITS CODING SEQUENCE, THEIR APPLICATION AND METHODS OF PRODUCTION

RELATED APPLICATIONS

This is a continuation-in-part of and claims benefit under 35 U.S.C. §120 of International Patent Application No. PCT/PL2004/00003 filed on Apr. 30, 2004, which claims benefit under 35 U.S.C. §119 of Polish Patent Application No. P.359813 filed on May 2, 2003, the content of both applications are incorporated herein by reference.

BACKGROUND OF THE INVENTION

The present invention relates to a UBP1 protease mutant and the sequence coding it, their application as well as products and methods for their production. The present invention is used in the production of recombinant proteins, particularly on an industrial scale.

Ubiquitin is a protein commonly expressed in eukaryotes. It has been shown that it is a useful carrier for heterologous proteins obtained through expression in Escherichia coli (R. Baker, Current Opinion in Biotechnology 1996, 7:541-546). Ubiquitin is composed of 76 amino-acid residues, with a combined molecular mass of 8.8 kDa. This protein is an element of the universal protein modification system. Ubiquitination is involved in almost all metabolic processes, from cell division to its death. Ubiquitin is involved in the regulation of gene expression, DNA repair, and it influences chromatin activity. It takes part in oncogenesis. It also plays a pivotal role in the proteolysis of regulatory proteins with short half-lives, and proteins with longer half lives as well, which must be removed from a cell for various reasons.

Protein ubiquitination does not occur in bacteria. It has been shown that proteins fused to ubiquitin undergo greater expression in E. coli, and are more stable. Crystallographic analysis of ubiquitin using nuclear magnetic resonance demonstrated that both in solid state and in aqueous solution ubiquitin maintains a dense, globular structure (S. Vijay-Kumar, C. Bugg, W. Cook, J. Mol. Biol. 1987, 194:531-544). The hydrophobic core of ubiquitin is composed of five parallel lengths of the peptide chain, held together with regularly spaced hydrogen bonds, forming a so-called β-pleated sheet. Its surface edges are joined with short chain lengths, coiled into 3.5 turns of an α-helix. Such a structure gives ubiquitin an uncommon resistance to high temperatures, a wide range of pH and polarity changes in the environment (Harding M M, Williams D H, Woolfson D N Biochemistry 1991, 30:3120-3128).

The UBP1 protease is an enzyme isolated from yeast, which severs ubiquitin from a protein located at its C-end. The enzyme was described in 1991 (J. Tobias, A. Varshavsky, J. Biol. Chem. 1991, 266; 12021-12028) and is a subject of patent application WO91/17245 (European Patent EP 531 404). Its activity has been studied, and its culture conditions have been described in E. coli. In accordance to the contents of the description, it is a cysteine protease, which binds ubiquitin with an ester bond. UBP1 is made up of an 809 amino-acid chain. The enzymatic activity depends on its ability to sever the ubiquitin peptide from the polypeptide found at its C-end, regardless of the amino-acid sequence at the N-end of the ubiquitin.

Application WO93/09235 describes other yeast proteins belonging to the same protease family, namely UBP2 and UBP3. This proteins show a similar activity (see also U.S. Pat. No. 5,494,818, U.S. Pat. No. 5,212,058, U.S. Pat. No. 5,683,904).

No improved mutants of UBP1 have been shown to date.

Expression systems are known, which yield fusion proteins composed of ubiquitin or its derivative and a polypeptide of interest. These then apply an enzyme which removes the ubiquitin (ie. UBP1), and recover the protein of interest (for examples see U.S. Pat. No. 5,132,213, U.S. Pat. No. 6,018, 102). Such a method contains many advantages, encompassing among others an improvement in the quality and yield efficiency of the protein, and a simplification of the purification process of the protein, a significant feature for the industrial production of recombinant proteins (for an example see WO03/010204). Using an enzyme which removes ubiquitin along with appropriately designed fusion proteins, one may also obtain N-modified polypeptides (for example U.S. Pat. No. 5,847,097).

The application of an enzyme which removes ubiquitin in technological processes requires large amounts of this enzyme. Known methods, however, are not conducive to the efficient expression of said enzyme, and significantly limit the possibilities of its application, particularly in industrial processes.

SUMMARY OF THE INVENTION

The goal of the present invention is to obtain an efficient method for the production of a protein for severing ubiquitin and the means for its realisation. A particular goal of the present invention is to obtain the means to produce a protein exhibiting UBP1 activity more easily.

Thus, the goal of this invention is to also obtain a nucleotide sequence facilitating the efficient expression of an enzyme with UBP1 activity. Thus, the goal of the present invention is to also obtain a new, improved polypeptide comprising a protein with UBP1 activity.

Unexpectedly, the above goals were met thanks to the present invention.

A subject of the present invention is a mutant of the UBP1 protease, which contains an amino-acid sequence containing at least one of the following modifications:

a substitution of proline at position 415 of the UBP 1 sequence with leucine,
  a substitution of phenyloalanine at position 739 of the UBP1 sequence with leucine,
  a substitution of glutamine at position 754 of the UBPI sequence with leucine,
  fusion of the polypeptide sequence of ubiquitin to an N-terminal amino-acid with a peptide bond,
  deletion of at least a portion of the amino-acids in positions from 1 through 54 of the UBP1 sequence.

Preferentially, the deletion encompasses all amino-acids in positions from 1 through 54 of the UBPI sequence. In accordance with the particularly preferential embodiment of the present invention mutant, a protease according to the present invention possess one of the amino-acid mutant sequences presented in FIGS. 6, 8-10.

A subject of the present invention is also the nucleotide sequence coding a UBP1 protease mutant, characterised in that it contains at least one of the following mutations:

a substitution of the proline codon at position 415 of the UBP 1 amino-acid sequence with a leucine codon,
  a substitution of the phenyloalanine codon at position 739 of the UBP1 amino-acid sequence with a leucine codon,
  a substitution of the glutamine codon at position 754 of the UBP1 amino-acid sequence with a leucine codon, fusion of the sequence coding ubiquitin, preferentially in the starting region of the open reading frame, deletion of at least a portion of the first 54 codons of the sequence coding UBP1. Preferentially, the deletion encompasses the initial 132 nuclotides.

Preferentially, the nucleotide sequence according to the present invention also contains codon changes accounting for the requirements of the planned expression system. In a particularly preferential embodiment the expressing host is *E. coli*, and the codon changes encompass the substitution of at least one of the arginine codons in positions 96, 476, 482, 487, 702, 705, 710, 796, 801 of the UBP1 amino-acid sequence with the the CGT or CGC codon.

In one preferential embodiment, the nucleotide sequence according to the present invention contains one of the nucleotide sequences presented in FIGS. 1, 5, 8-10.

Another subject of the present invention is the application of the UBP1 protease mutant in the production of the enzyme which severs ubiquitin, where the mutant contains the characteristics defined above. Preferentially, the obtained enzyme which severs ubiquitin is used to produce a protein of interest from a hybrid protein composed of ubiquitin and the protein of interest. The protein of interest is a medicinal protein, preferentially interleukin, interferon, growth hormone, insulin or erythropoetin.

The next subject of the present invention is the application of a nucleotide sequence coding the UBP1 protease mutant to obtain an enzyme which severs ubiquitin, where a sequence is used according to the present invention, as defined above.

A subject of the present invention is also the expression vector which contains the nucleotide sequence coding the UBP1 protease mutant according to the present invention, as defined above. Preferentially, the nucleotide sequence coding the UBP1 protease mutant is contained in the pT7-7ArgStop plasmid.

A subject of the present invention is also a host cell transformed with an expression vector containing a nucleotide sequence coding the UBP1 protease mutant according to the present invention, as defined above.

A subject of the present invention is also a method for the production of a protein which severs ubiquitin, characterised in that the host cells which have been transformed with the expression vector containing the nucleotide sequence coding the UBP1 protease mutant are cultured, and the desired enzyme or fraction containing it is isolated, where the nucleotide sequence coding the UBP1 protease mutant is a sequence according to the present invention, as defined above.

Unexpectedly, it turned out that the new UBP1 mutants proposed in the present invention retain the basic enzymatic activity of severing ubiquitin, and are easier to produce. The presented means facilitate the easy and efficient expression of an enzyme with UBP1 activity, for example in the well understood system based on *E. coli* cells. Thanks to this, mutants according to the present invention are suitable for industrial application, for example in the process of synthesis of recombinant proteins, encompassing the expression of fusion proteins containing ubiquitin.

BRIEF DESCRIPTION OF THE DRAWINGS

To better illustrate the nature of the present invention, the description includes the following figures:

FIG. 1 (SEQ ID NO.: 1) represents the sequence coding the hybrid protein Ubiquitin::UBP1 (lower case letters describe the ubiquitin sequence, the UBP1 sequence is in upper case, bold print marks the SacII recognition sequence, the stop codon and the sites of primers UBP1MG and UBP1MD);

FIG. 5 (SEQ ID NO: 3) The sequence coding the hybrid protein UBI::UBP1 ΔC with the transmembrane domain removed (lower case denotes the UBI sequence, upper case denotes the UBP1 ΔC protease coding sequence)

FIG. 6 (SEQ ID NO: 5) The amino-acid sequence of the UBP1 protease, and the proposed changes. The sequence of the removed transmembrane fragment is in bold. The active centre is in underlined italics, whereas amino-acids substituted with leucine, called by us mutations A, B and C are in bold underlined type.

FIG. 8 (SEQ ID NO: 6 and SEQ ID NO: 7) The nucleotide and amino-acid sequence of UBI+UBP1ABC, the mutations are substitutions of: proline for leucine (position 493), phenyloalanine for leucine (position 814) and glutamine for leucine (position 829); amino-acid residues are marked with bold, underlined type.

FIG. 9 (SEQ ID NO: 8 and SEQ ID NO: 9) The nucleotide and amino-acid sequence of UBI+UBP1BC, the mutations are substitutions of: phenyloalanine for leucine (position 814) and glutamine for leucine (position 829); amino-acid residues are marked with bold, underlined type.

FIG. 10 (SEQ ID NO: 10 and SEQ ID NO: 11) The nucleotide and amino-acid sequence of UBI+UBP1C, the mutation is a substitution of glutamine for leucine (position 829); the amino-acid residue is marked with bold, underlined type.

DETAILED DESCRIPTION OF THE INVENTION

The following examples are only meant to present assorted embodiments of the present invention and should not be viewed as the whole of its scope.

Example 1

Mutants of the UBP1 Protein

Example UBP1 mutants containing point mutations:

I UBP1ABC with the A, B, C mutation, a substitution of proline, phenyloalanine and glutamine with leucine at positions 415, 739 and 754 respectively.

II UBP1BC with mutations at positions 739 and 754, substitutions phenyloalanine and glutamine respectively with leucine, III UBP1C a mutation at position 754, a substitution of glutamine with leucine. Using these mutants, hybrid proteins were designed which additionally contain the ubiquitin amino-acid sequence at the N-end (proteins: UBI+UBP1ABC, UBI+UBP1BC and UBI+UBP1C).

The next group of mutants was produced by deleting the transmembrane domain of UBP1 or a portion thereof from the above proteins (example proteins: UBP1ΔC, UBI+UBP1ΔC and their mutants containing at least one of the mutations A, B or C).

A1 mutations are located outside of the active centre, composed of cysteine (100-117 aa) and histidine (681-725 aa) residues, marked with underlined italics in FIG. 6 which represents the amino-acid sequence of UBP1 with the modified portions indicated.

The above mentioned protease variants were used as an enzyme severing ubiquitin from proteins fused to its C-end. In our case it was the hybrid UBI: Interferon α.

Example 2

Construction of a Plasmid with the UBP1 Protease Gene and its Mutants

The UBP1 protease gene, 2430 base pairs long, was obtained using PCR. The template used was genomic DNA of *Saccharomyces cerevisiae*, strain W303 (ade2-1, leu2-3, 112, trp1-1, his3-11, ura3-1, mit+, rho+). For amplification, the following primers were designed:

```
UBP1P
    SacII
5' AGACTCCGCGGTGGTGATTTGTTTATTGAAA (SEQ ID NO: 12)
GCAAGATA

UBP1K
    BamHI
5' GGGGGATCCTTAGTTTACATCTTTACCAGAAA (SEQ ID NO: 13)
TA
```

Figure 2:
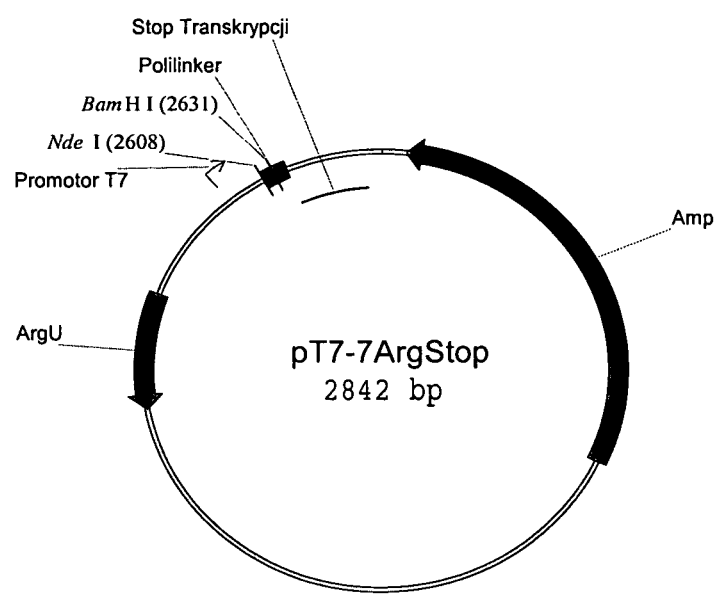
FIG. 2 represents a map of the pT7-7ArgStop expression vector, where Amp is the ampicillin resistance gene, ArgU is a gene coding tRNA complementary to the AGA codon, Stop Transkrypcji is a transcription stop nucleotide sequence from the φ10 gene of the T7 phage.

The oligonucleotides contained recognitions sites for the restriction endonucleases SacII and BamHI. The amplified DNA fragment was ligated with the pBluescript SK(−) vector, digested with the same enzymes. The ligation mixture was used to transform competent *E. coli* cells, strain NM522. Plasmid DNA was isolated using the alkaline method. Next, the 2430 bp UBP1 gene was excised from the recombinant using the restriction enzymes SacII and BamHI. DNA obtained in this way was ligated with the expression vector pT7-7ArgStopUBI, which was created by ligating the 240 bp ubiquitin gene sequence into the pT7-7ArgStop plasmid (FIG. 2) into NdeI and EcoRI restriction sites. The PT7-7ArgStop plasmid was created in the laboratory of Prof. Dr. hab. Andrzej Plucienniczak, based on the pT7-7 plasmid (S. Tabor, C. Richardson, *Proc. Nat. Acad. Sci.* 1985,262:1074-1078).

The pT7-7ArgStopUBI vector was digested with the SacII and BamHI enzymes, and then ligated with the DNA fragment coding UBP1. The ligation mixture was used to transform the competent *E. coli* strain DH5α. The DNA was then isolated, and the sequence was determined, shown in FIG. 1.

Figure 4:
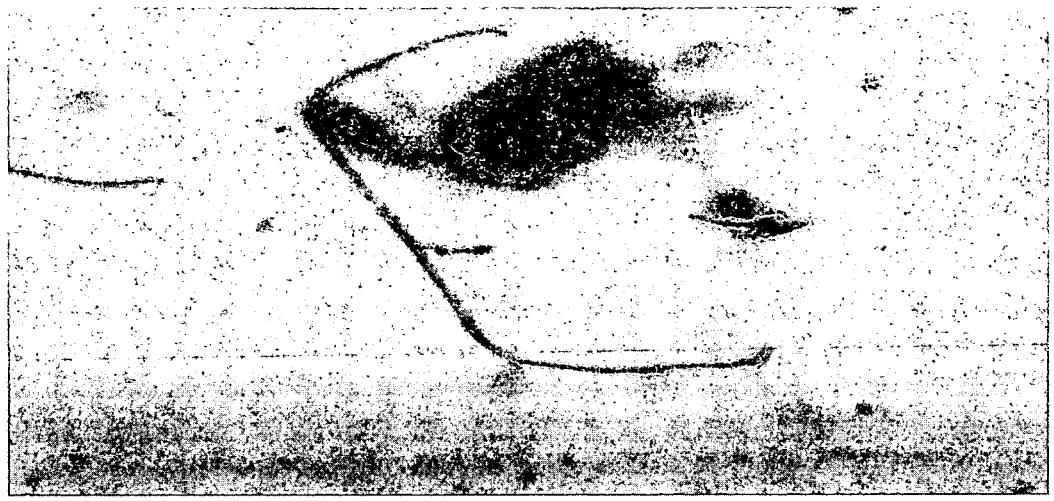
FIG. 4 represents a micrograph of Gramm-stained BLD21 *E. coli* cells containing the plasmid pT7-7ArgStop UBI+UBP1.

The protease gene was included into the expression vector pT7-7ArgStopUBI. The obtained plasmids with the hybrid gene UBI::UBP1 were used to transform BLD21 *E. coli* bacteria. The protein UBP1 was synthesized (produced) while these bacteria were cultyred. The culture was maintained at 25° C. in LB medium with an addition of 50 mg/ml of ampicillin. 30 hours were required for the culture to reach an $OD_{600}=1$. Gramm-stained slides were made. It turned out that the *E. coli* bacteria were several dozen times longer than usual (FIG. 4).

Figure 3:
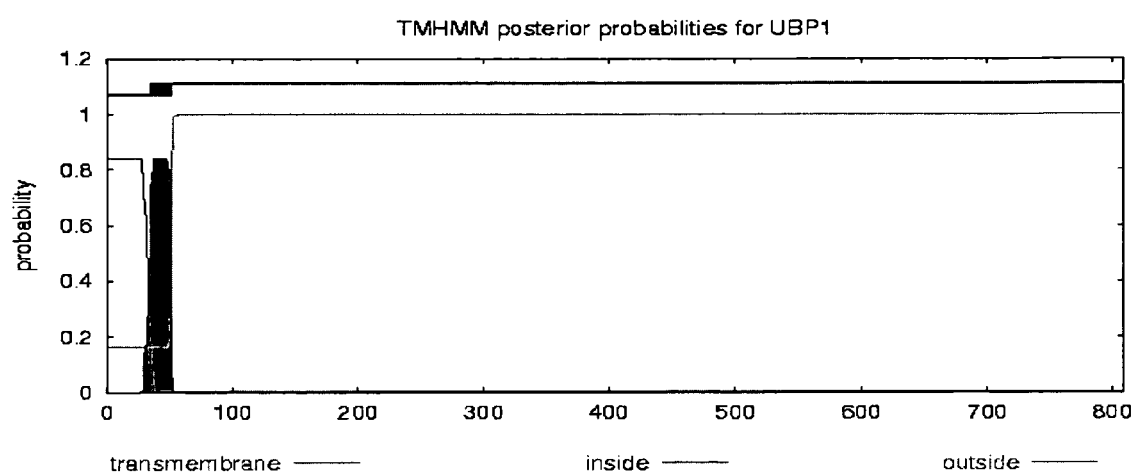
FIG. 3 represents a probability curve for the existence of a transmembrane domain in UBP1, obtained using the TMHMM Prediction of transmembrane helices in proteins (CBS; Denmark) package; a 51 amino-acid transmembrane domain was noted.

The UBP1 sequence was examined using the TMHMM software package, which determines the likelihood of the existence of a transmembrane domain (FIG. 3). The domain discovered could retard bacterial growth and cell division. This might have been the cause of the long time it took for the growth to reach $OD_{600}=1$.

PCR was used to remove this domain from the UBP1 gene. The modification was based on inserting an additional SacII restriction site into the sequence coding UBP1.

Primers were designed for this reason, which were used in for point mutagenesis using the "QuikChange Site-Directed Mutagenesis Kit" from Stratagene:

```
UBP1MG
       SacII
5' GGCATAGTAGTATTTTTTACCGCGGTGGTG (SEQ ID NO: 14)
ACCATCTAAACTACATTGT

UBP1MD
       SacII
5' ACAATGTAGTTTAGATGGTCACCACCGCGGT (SEQ ID NO: 15)
AAAAAAATACTACTATGCC
```

Using the UBP1MG and UBP1MD primers (marked in bold in FIG. 1), recognition sequences for the SacII enzyme (underlined) were inserted into the interior of the UBP1 coding sequence. Thanks to this a 169 bp fragment was removed during the digestion of the pT7-7ArgStopUBI+UBP1 plasmid with the SacII restrictase. This resulted in a new plasmid, which we designated pT7-7ArgStopUBI+UBP1ΔC. It contains the coding sequence shown in FIG. 5. Other plasmids coding alternate hybrid mutants according to the present invention containing the UBI sequence were produced in an analogous fashion.

Example 3

Expression of the UBP1ΔC Protease and Enzyme Purification

Figure 7:
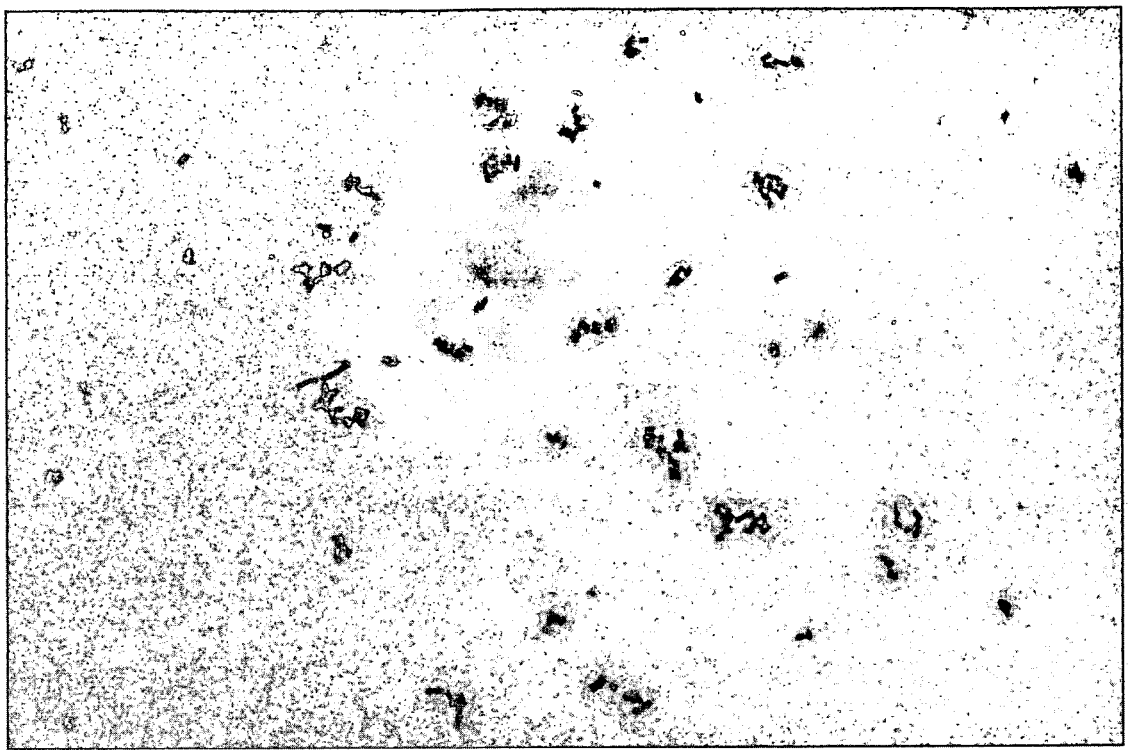
FIG. 7 A micrograph representing an in vivo preparation of a BLD21 *E. coli* culture with the plasmid pT7-7ArgSto-pUBI+UBP1ΔC with exchanged ariginine codons.

BLD21 *E. coli* bacteria were transformed with a plasmid containing the UBP1 protease gene, or one of its mutants. During the culturing it was determined that the removal of the transmembrane domain facilitated the culturing, and shortened the time from 30 to about 12 hours. It was also observed that the cells producing the mutant according to the present invention returned to the original shape (FIG. 7).

Figure 11:
FIG. 11 Examination of the activity of the mutants obtained, digestion products: electrophoretic separation in polyacrylamide gel with SDS. From the left, the lanes are: lane No. 1, molecular mass marker (from the top 97, 66, 45, 30, 20.1, 14.4 [kDa]); lanes 2 and 3, digestion of UBI::INF with the UBP1ΔC protease over 2 h at 37° C.; lane 4, undigested UBI::INF; lanes 5 and 6, UBI::INF digested with the UBP1ΔC protease over 1 h at 37° C.

BLD21 *E. coli* bacteria containing the appropriate plasmid were cultured on LB medium containing ampicillin (50 mg/ml) at 25° C. over 12 h until $OD_{600}=1$, and subsequently induced with the addition of IPTG (isopropylthiogalactoside). After 2.5 h, the bacteria were centrifuged. The cell pellet was suspended in lysis buffer, and incubated for 30 min. at 20° C. Triton X-100 was added to a final concentration of 1%. The mixture was sonificated and centrifuged. The supernatant was applied to an SP column (the strong cationite Sepharose FF) and subsequently to a hydrophobic Phenylo Sepharose FF column. The protease activity was measured via the digestion of UBI::Interferonoc with purified enzyme fractions. The results are presented in FIG. 11.

Additionally, the UBP1 protease gene was modified through the exchange of certain arginine codons unfavourable to *E. coli* (AGA or AGG) for codons which occur in these bacteria *E. coli* (CGT or CGC). In the ultimate version, the arginine codons at positions 96, 476, 482, 487, 702, 705, 710, 796 and 801 were replaced, marked in bold in FIG. 6.

What is claimed is:

1. A ubiquitin protease-1 (UBP1) mutant comprising an amino acid sequence having at least one of the following modifications in the UBP1 sequence of SEQ ID NO:5:
   (a) a proline to leucine substitution at position 415 of the UBP1 sequence;
   (b) a phenylalanine to leucine substitution at position 739 of the UBP1 sequence;
   (c) a glutamine to leucine substitution at position 754 of the UBP1 sequence;
   (d) a fusion of a ubiquitin polypeptide to the N-terminal amino-acid of the UBP1 sequence with a peptide bond; and
   (e) deletion of at least a portion of the amino acid from positions 1 through 54 of the UBP1 sequence.

2. The mutant of claim 1, wherein the deletion encompasses all amino-acids found at positions 1 through 54 of the UBP1 sequence of SEQ ID NO:5.

3. The mutant of claim 1, wherein the mutant comprises an amino acid sequence selected from the group consisting of SEQ ID NOS:5, 7, 9 and 11.

4. A method of severing ubiquitin from a hybrid protein wherein the hybrid protein comprises ubiquitin and a protein or polypeptide of interest, comprising:

bringing a UBP1 protease mutant into contact with the hybrid protein, wherein the mutant applied comprises an amino-acid sequence having at least one of the following modifications in the amino acid sequence of SEQ ID NO:5:
   (a) a proline to leucine substitution at position 415 of the UBP-1 sequence;
   (b) a phenylalanine to leucine substitution at position 739 of the UBP-1 sequence;
   (c) a glutamine to leucine substitution at position 754 of the UBP1 sequence;
   (d) a fusion of a ubiquitin polypeptide to the N-terminal amino-acid of the UBP1 sequence with a peptide bond; and
   (e) deletion of at least a portion of the amino acids from positions 1 through 54 of the UBP-1 sequence.

5. The method of 4, wherein the deletion encompasses all amino acids at positions 1 through 54 of the UBP-1 sequence.

6. The method of claim 4 wherein the UBP-1 protease mutant is used to produce proteins of interest from hybrid proteins comprising ubiquitin and a protein of interest.

7. The method of claim 6 wherein the protein of interest is selected from the group consisting of interleukin, interferon, growth hormone, insulin, and erythropoietin.

8. The method of claim 4, wherein the mutant comprises an amino acid sequence selected from the group consisting of SEQ ID NOS:5, 7, 9 and 11.

* * * * *